(12) United States Patent
Gao et al.

(10) Patent No.: US 7,514,237 B2
(45) Date of Patent: Apr. 7, 2009

(54) SYSTEMS AND METHODS FOR PROTEIN PRODUCTION

(75) Inventors: Yijie Gao, Brookline, MA (US); Nicole M. Piche, Waltham, MA (US); Mei Geng, Bedford, MA (US); Stephen H. Herrmann, Stowe, MA (US); Xiaotian Zhong, Wayland, MA (US); Ronald Kriz, Northborough, MA (US); Zhijian Lu, Bedford, MA (US)

(73) Assignee: Wyeth, Madison, NJ (US)

( * ) Notice: Subject to any disclaimer, the term of this patent is extended or adjusted under 35 U.S.C. 154(b) by 145 days.

(21) Appl. No.: 11/217,137

(22) Filed: Sep. 1, 2005

(65) Prior Publication Data

US 2006/0053502 A1 Mar. 9, 2006

Related U.S. Application Data

(60) Provisional application No. 60/606,439, filed on Sep. 2, 2004.

(51) Int. Cl.
*C12P 21/06* (2006.01)
*C12N 1/20* (2006.01)

(52) U.S. Cl. ............... 435/69.1; 435/252.3; 435/325

(58) Field of Classification Search ............ 435/252.3, 435/69.1, 320.1, 253.6, 325
See application file for complete search history.

(56) References Cited

U.S. PATENT DOCUMENTS

| 6,537,542 | B1 | 3/2003 | Treco et al. |
| 6,541,231 | B1 | 4/2003 | Baszczynski et al. |
| 6,656,727 | B2 | 12/2003 | Gunzburg et al. |
| 2001/0034045 | A1 | 10/2001 | Penttila et al. |
| 2005/0250182 | A1* | 11/2005 | Kaufman et al. ........... 435/69.1 |

FOREIGN PATENT DOCUMENTS

WO 2004/111194 A2 12/2004

OTHER PUBLICATIONS

Flintoff, W. F. et al., Isolation and partial characterization of three methotrexate-resistant phenotypes from Chinese hamster ovary cells, *Somatic Cell Genet.*, 2(3):245-261, 1976.
Graf, L. H., Jr. et al., Direct demonstration of genetic alterations at the dihydrofolate reductase locus after gamma irradiation, *Mol. Cell Biol.*, 2(1):93-96, 1982.
Kao, F.-T. and Puck, T. T., Genetics of somatic mammalian cells, VII. Induction and isolation of nutritional mutants in Chinese hamster cells, *Proc. Natl. Acad. Sci. USA*, 60(4):1275-1281, 1968.
Kaufman, R. J. et al., Evolution of chromosomal regions containing transfected and amplified dihydrofolate reductase sequences, *Mol. Cell Biol.*, 3(4):699-711, 1983.
Urlaub, G. et al., Deletion of the diploid dihydrofolate reductase locus from cultured mammalian cells, *Cell*, 33(2):405-412, 1983.

Yoshida, H. et al., XBPI mRNA is induced by ATF6 and spliced by IRE1 in response to ER stress to produce a highly active transcription factor, *Cell*, 107(7):881-891, 2001.
Gunn et al., (2004), "A Role for the Unfolded Protein Response in Optimizing Antibody Secretion," *Molecular Immunology*, 41(9):919-27.
Shuda et al., "Activation of the ATF6, XBP1 and grp78 genes in human hepatocellular carcinoma: a possible involvement of the ER stress pathway in hepatocarcinogenesis," *Journal of Hepatology* 38 (2003) 605-614.
PCT International Search Report of Aug. 23, 2006 for International Application No. PCT/US2005/031081, 7 pgs.
PCT Written Opinion of the International Searching Authority for International Application No. PCT/US2005/031081, 5 pgs.
Altschul, S.F. et al., Basic local alignment search tool, *J. Mol. Biol.*, 215(3):403-410, 1990.
Binz, H. K. et al., High-affinity binders selected from designed ankyrin repeat protein libraries, *Nat. Biotechnol.*, 22(5):575-582, 2004.
Calfon, M. et al., IRE1 couples endoplasmic reticulum load to secretory capacity by processing the XBP-1 mRNA, *Nature*, 415(6867):92-96, 2002, erratum in: *Nature* Nov. 14, 2002;420(6912):202.
Haze, K. et al., Mammalian transcription factor ATF6 is synthesized as a transmembrane protein and activated by proteolysis in response to endoplasmic reticulum stress, *Mol. Biol. Cell.*, 10(11):3787-3799, 1999.
Lipovsek, D. and Pluckthun, A., In-vitro protein evolution by ribosome display and mRNA display, *J. Immunol. Methods*, 290(1-2):51-67, 2004, erratum in *J. Immunol. Methods*, 294(1-2):213, 2004.
Myers, E. and Miller, W., Optimal alignments in linear space, *Comput. Appl. Biosci.*, 4(1):11-17, 1988.
Needleman, S. B. and Wunsch, C.D., A general method applicable to the search for similarities in the amino acid sequence of two proteins, *J. Mol. Biol.*, 48(3):443-453, 1970.

(Continued)

*Primary Examiner*—Maryam Monshipouri
(74) *Attorney, Agent, or Firm*—Margo H. Furman; Choate, Hall & Stewart LLP

(57) ABSTRACT

The invention relates to systems and methods for producing proteins of interest. The invention employs genetically-engineered animal or plant cells that have modified protein folding or processing capacities. In one aspect, the invention features genetically-engineered cells comprising one or more recombinant expression cassettes which encode (1) a protein of interest and (2) a polypeptide that is functional in the unfolded protein response (UPR) pathway of the cells. Co-expression of the polypeptide significantly increases the yield of the protein of interest in the genetically-engineered cells. In one example, the genetically-engineered cells are animal cells, and the co-expressed polypeptide is a component or modulator of an XBP1- or ATF6-mediated UPR pathway.

17 Claims, 9 Drawing Sheets

OTHER PUBLICATIONS

Sinacore, M. S. et al., CHO DUKX cell lineages preadapted to growth in serum-free suspension culture enable rapid development of cell culture processes for the manufacture of recombinant proteins, *Biotechnol. & Bioengineering*, 52(4):518-528, 1996.

Urlaub, B. and Chasin, L. A., Isolation of Chinese hamster cell mutants deficient in dihydrofolate reductase activity, *Proc. Natl. Acad. Sci. USA*, 77(7):4216-4220, 1980.

Williams, G. et al., Overcoming the inhibitors of myelin with a novel neurotrophin strategy, *J. Biol. Chem.*, 280(7):5862-5869, 2005.

Lee, et al., *Moll. Cell. Biol.*, 23(21):7448-7459, 2003.
Ma, et al., *Cell*, 107:827-830, 2001.
Martinez, et al., *Plant Cell*, 15:561-576, 2003.
Shen, et al., *Cell*, 107:893-903, 2001.
Valkonen, et al., *Appl. Environ. Microbiol.*, 69(4):2065-2072, 2003.
Sriburi, et al., *J. Cell Biol.*, 167(1):35-41, 2004.
Ng, et al., *J. of Cell Biol.*, 150(1):77-88, 2000.
Brewer, et al., *Nat. Immunol.*, 6(1):23-29, 2005.

* cited by examiner

SYSTEMS AND METHODS FOR PROTEIN PRODUCTION

This application claims the benefit of U.S. Provisional Application No. 60/606,439 filed Sep. 2, 2004.

TECHNICAL FIELD

The invention relates to expression systems and methods of using the same for producing proteins of interest.

BACKGROUND

Secreted and membrane proteins undergo folding and other post-translational modifications in the endoplasmic reticulum (ER)-Golgi system. Disruption of the homeostasis of this system causes cellular stress that can lead to apoptosis. ER homeostasis can be altered by changes in $Ca^{2+}$ concentration or redox status, altered glycosylation, or accumulation of unfolded or misfolded proteins in the ER lumen. To overcome stress, the secretory system has evolved an adaptive stress response mechanism known as the unfolded protein response (UPR). Activation of the mammalian UPR results in at least three responses: (1)' the amount of new protein translocated to the ER lumen is reduced through reduction in translation; (2) accumulated protein in the ER lumen is retrotranslocated to the cytosol and degraded; and (3) the ER-Golgi secretory system is remodeled so that the protein folding and processing capacities in the system are enhanced.

The capacity enhancement of the ER-Golgi system in response to stress involves upregulation of folding and processing enzymes. These enzymes include ER chaperones, enzymes involved in glycosylation and disulfide bond formation, and enzymes participating in vesicle transportation. In mammalian cells, IRE1 and ATF6 proteins are the major transducers of this branch of the UPR pathway. IRE1 protein is an ER transmembrane glycoprotein with kinase and endonuclease activities at its C-terminal cytosolic domain. At least two IRE1 genes have been identified in mice, IRE1α and IRE1β. IRE1α is essential for viability and is broadly expressed. IRE1β has been detected only in the gastrointestinal mucosa. ER stress leads to oligomerization of IRE1 proteins and trans-autophosphorylation of their cytosolic domains. Phosphorylation of IRE1 activates its endonuclease activity which excises an intron from the mRNA of the transcription factor X-box binding protein 1 (XBP1). This splicing event results in the conversion of a transcription-inactive XBP1 isoform (i.e., XBP1u) to a transcription-active XBP1 isoform (i.e., XBP1s or XBP1p). XBP1p then travels into the nucleus, where it binds to its target sequences including ER stress response element (ERSE) and UPR element (UPRE), in the regulatory regions of ER-Golgi chaperone/enzyme genes, to induce their transcription. Many UPR target genes have one or more copies of ERSE or UPRE sequence in their promoter regions.

ATF6 (activating transcription factor 6) is another ER transmembrane protein. ER stress leads to the transit of ATF6 protein to the Golgi compartment where its cytosolic domain is cleaved by Site 1 and Site 2 proteases. The cleaved cytosolic domain travels to the nucleus and acts as a transcription factor by binding to ERSE sequences, which in turn upregulates a variety of chaperones and processing enzymes in the secretory pathway.

Activation of the UPR pathway in mammalian cells also leads to a transient inhibition of protein translation through the PERK signaling pathway. PERK is an ER transmembrane kinase which can phosphorylate the eukaryotic translation initiation factor eIF2α in response to ER stress. Phosphorylation of eIF2α prevents the assembly of the 43S ribosomal pre-initiation complex and therefore results in translation attenuation. Paradoxically, phosphorylation of eIF2α also results in rapid synthesis of transcription factor ATF4, which in turn enhances the expression of a proapoptotic transcription factor CHOP. CHOP potentiates cell death when the detrimental effects of ER stress can no longer be overcome.

Overexpression of secreted recombinant proteins in mammalian cells often leads to low production yield. A commonly used method to improve protein production is to increase the transcriptional rates, such as using stronger promoters or increasing gene copy numbers. However, increased transcriptional rates may exacerbate ER stress and, therefore, often fails to significantly improve the yield. In some cases, it may even further reduce the production yield.

SUMMARY OF THE INVENTION

The present invention provides expression systems with improved production yields for secreted or membrane proteins. The systems employ genetically-engineered animal or plant cells that have modified, and in many cases, enhanced protein folding or processing capacities.

In one aspect, the present invention features genetically-engineered animal or plant cells comprising one or more recombinant expression cassettes which encode (1) a protein of interest and (2) a component or modulator of a UPR pathway. Suitable UPR components or modulators include, but are not limited to, non-IRE1 molecules that are functional in the UPR pathways. They can be endogenous UPR components of the host cells, or variants or functional equivalents thereof. They can also be naturally occurring or non-naturally occurring molecules that modulate the activity or expression of an endogenous UPR component either directly or indirectly. In many cases, the UPR components/modulators are selected such that their expression or activation increases the protein folding or processing capacity of the host cells.

Exemplary UPR components/modulators include, but are not limited to, transcription factors, such as XBP1 or ATF6 or their biologically active fragments or variants. Other components in the XBP1- or ATF6-mediated UPR pathways can also be used. In addition, ER-resident chaperones or processing enzymes can be used.

Proteins that can be produced according to the present invention include, but are not limited to, erythropoietins, growth hormones, insulins, interferons, growth factors, membrane proteins, or other therapeutic, prophylactic or diagnostic proteins. In many embodiments, the proteins of interest are expressed by the host cells as secreted or membrane proteins.

The genetically-engineered cells of the invention can be derived from cell lines, primary cultures, or other isolated or cultured cells. The genetically-engineered cells can also be hybrid cells. In many cases, the hybrid cells are generated by fusing an animal cell and a cancer cell (such as a myeloma cell). Recombinant expression cassettes encoding a protein of interest or a UPR component/modulator can be incorporated or introduced into the hybrid cells before or after the fusion event. In addition, the genetically-engineered cells of the present invention can be cells of transgenic animals or plants. In one embodiment, the genetically-engineered cell is a mammalian cell.

A recombinant expression cassette can be incorporated into a host cell by a variety of means. For instance, an expression cassette can be stably integrated into a chromosome or the genome of a host cell. The integration can be either random or targeted (e.g., by using the Cre-lox recombination system of bacteriophage P1). An expression cassette can also be introduced into a host cell via a non-integrated expression vector.

A recombinant expression cassette can be controlled by a constitutive or inducible promoter. It can also be controlled by a tissue-specific or developmentally-regulated promoter. Other types of promoters can also be used for the present invention.

In another aspect, the present invention features genetically-modified animal or plant cells comprising one or more recombinant expression cassettes which encode (1) a protein of interest and (2) a polypeptide capable of binding to a UPRE or ERSE of the host cells. In one embodiment, the UPRE- or ERSE-binding polypeptide is a transcription factor, such as XBP1 or ATF6. In another embodiment, the UPRE- or ERSE-binding polypeptide can recruit another protein to the promoter regions of UPR genes, and the latter protein comprises a transactivation domain capable of activating the transcription of the UPR genes (e.g., the transcription activation domain of XBP1 or ATF6).

A genetically-engineered cell of the invention can express a protein of interest and a UPR component/modulator from the same or different recombinant expression cassettes. The protein of interest and the UPR component/modulator can be controlled by the same or different promoters.

In one embodiment, a genetically-engineered cell of the invention comprises (1) a first recombinant expression cassette encoding a protein of interest and (2) a second recombinant expression cassette encoding a UPR component or modulator or a UPRE or ERSE binding protein (e.g., XBP1 or ATF6). The ratio of the total number of the first recombinant expression cassette over the total number of the second recombinant expression cassette in the cell can range, without limitation, from no more than 0.1:1 to at least 10:1. In many instances, the promoter employed by the first recombinant cassette can have the same or similar strength as the promoter employed by the second recombinant cassette, and the ratio of the total number of the first recombinant cassette over the total number of the second recombinant cassette ranges from 0.5:1 to 10:1 (such as at least 1:1, 2:1, 3:1, 4:1, 5:1, 6:1, 7:1, 8:1, or 9:1). The promoters in the first and the second recombinant cassettes can also have different strengths. For instance, the promoter in the first recombinant cassette can be stronger than the promoter in the second recombinant cassette, such as by at least 2, 3, 4, 5, 6, 7, 8, 9, 10, or more folds.

In still another aspect, the present invention features animals or plants which include a genetically-engineered cell of the present invention. Methods for incorporating a genetically-modified cell into an animal or plant are well known in the art. In many embodiments, the animals or plants are transgenic animals or plants.

In yet another aspect, the present invention features cell cultures that are transfected or transduced with one or more expression vectors encoding (1) a protein of interest and (2) a component or non-IRE1 modulator of a UPR pathway. In many embodiments, the expression vector(s) comprises a first recombinant expression cassette encoding the protein of interest and a second recombinant expression cassette encoding the UPR component or modulator (e.g., XBP1 or ATF6). The first and the second expression cassettes can be carried by the same or different expression vectors. The molar ratio of the first recombinant expression cassette over the second recombinant expression cassette in the cell culture can range, for example, from no more than 0.1:1 to at least 10:1, such as at least 1:1, 2:1, 3:1, 4:1, 5:1, 6:1, 7:1, 8:1, 9:1, 10:1, or more. The cell culture can be a mammalian cell culture, an insect cell culture, a plant cell culture, or another culture that is suitable for the production of the protein of interest.

The present invention also features methods of using the genetically-engineered cells, animals, plants, or cell cultures for the production of proteins of interest.

In addition, the present invention features an expression vector which encodes (1) a protein of interest and (2) a component or non-IRE1 modulator of a UPR pathway.

Other features, objects, and advantages of the present invention are apparent in the detailed description that follows. It should be understood, however, that the detailed description, while indicating preferred embodiments of the invention, is given by way of illustration only, not limitation. Various changes and modifications within the scope of the invention will become apparent to those skilled in the art from the detailed description.

BRIEF DESCRIPTION OF THE DRAWINGS

The drawings are provided for illustration, not limitation.

DETAILED DESCRIPTION

Figure 1:
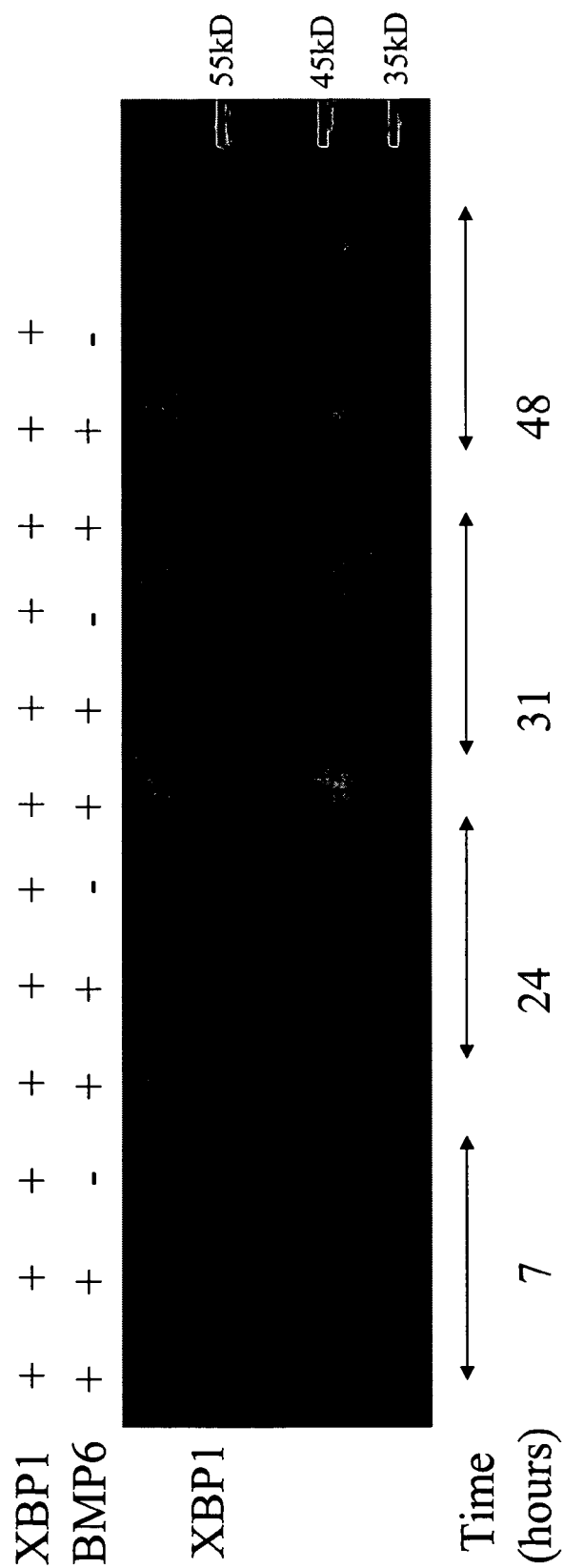
FIG. 1 demonstrates that overexpression of BMP6 in PA DUKX cells causes ER stress.

The present invention provides systems and methods for producing proteins of interest. The expression systems of the present invention employ genetically-engineered animal or plant cells that have modified or improved protein folding or processing capacities. In many embodiments, the genetically-engineered cells of the present invention comprise one or more recombinant expression cassettes which encode a protein of interest and a component or modulator of a UPR pathway. Co-expression of the UPR component/modulator significantly increases the yield of the protein of interest. UPR components/modulators suitable for the present invention include, but are not limited to, transcription factors, such as XBP1 or ATF6, or their biologically active fragments or variants. ER-associated chaperones or enzymes can also be used.

Various aspects of the present invention are described in further detail in the following subsections. The use of subsections is not meant to limit the invention. Each subsection may apply to any aspect of the invention. As used herein, the term "or" means "and/or" unless stated otherwise.

A. Proteins of Interest

Proteins that can be produced according to the present invention include, but are not limited to, therapeutic, prophylactic or diagnostic proteins, such as erythropoietins, growth hormones, insulins, interleukins, growth factors, interferons, colony stimulating factors, blood factors, vaccines, collagens, fibrinogens, human serum albumins, tissue plasminogen activators, glucosidases, alglucerases, myelin basic proteins, hypoxanthine guanine phosphoribosyl transferases, tyrosine hydroxylases, dopadecarboxylases, or antibodies. Exemplary antibodies amenable to the present invention include, but are not limited to, monoclonal antibodies, mono-specific antibodies, poly-specific antibodies, non-specific antibodies, humanized antibodies, human antibodies, single-chain antibodies, chimeric antibodies, synthetic antibodies, recombinant antibodies, hybrid antibodies, Fab, F(ab')$_2$, Fv, scFv, Fd, dAb, or functional fragments thereof. High-affinity binders selected using in vitro display technologies or evolutionary strategies can also be produced according to the present invention. These high-affinity binders include, but are not limited to, peptides, antibodies and antibody mimics. See, e.g., Binz, et al., NAT BIOTECHNOL., 22:575-582 (2004); and Lipovsek and Pluckthun, J IMMUNOL METHODS, 290:51-67 (2004). Other proteins of interest, such as kinases, phosphatases, G protein coupled receptors, growth factor receptors, cytokine receptors, chemokine receptors, cell-surface antibodies (membrane bound immunoglobulin), BMP/GDF-receptors, neuronal receptors, ion channels, proteases, transcription factors, or polymerases, can also be produced by the present invention.

In many embodiments, the proteins produced by the present invention are recombinant proteins. As used herein, a recombinant protein refers to a protein that is constructed or produced using recombinant DNA technology. A recombinant protein can have a naturally-occurring sequence or a genetically-engineered sequence. It can be expressed, for example, from a recombinant vector or from a gene that is endogenous to the host cells but has a genetically-engineered regulatory sequence. For instance, a recombinant protein can be produced from an endogenous gene but with a genetically-engineered viral promoter.

In many instances, the recombinant proteins are fusion proteins including a polypeptide tag to facilitate the isolation, purification, detection, immobilization, stabilization, folding, or targeting of the expressed products.

In many other instances, the recombinant proteins include signal peptides. A signal peptide can be endogenous or heterologous to the protein being produced. A signal peptide often determines whether a protein will be formed on the rough ER or on free ribosomes. A signal peptide can interact with signal recognition particle and direct the ribosome to the ER where co-translational insertion takes place. Many signal peptides are highly hydrophobic with positively charged residues. A signal peptide can be removed from the growing peptide chain by a signal peptidase, a specific protease located on the cisternal face of the ER.

Proteins targeted to the ER by signal sequences can be released into the extracellular space as secreted proteins. For example, vesicles containing secreted proteins can fuse with the cell membrane and then release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can be secreted into the extracellular space by proteolytic cleavage of a "linker" that holds the protein to the membrane.

A protein of interest can be isolated from an expression system by a variety of means. Examples of initial materials for protein isolation include, but are not limited to, culture medium or cell lysate. Suitable isolation methods include, but are not limited to, affinity chromatography (including immunoaffinity chromatography), ionic exchange chromatography, hydrophobic interaction chromatography, size-exclusion chromatography, HPLC, protein precipitation (including immunoprecipitation), differential solubilization, electrophoresis, centrifugation, crystallization, or a combination thereof. A polypeptide tag, such as a streptavidin tag, a FLAG tag, a poly-histidine tag, a glutathione S-transferase, or an Fc fragment, can be fused to a protein of interest to facilitate its isolation or purification. In one example, the polypeptide tag is cleavable from the protein of interest by a protease.

In many embodiments, a protein of interest isolated according to the present invention is substantially free from other proteins or contaminants. For instance, an isolated protein can be at least 50%, 60%, 70%, 80%, 90%, 95%, or 99% pure from other proteins. In one example, an isolated protein contains no more than an insignificant amount of contaminants that would interfere with its intended use.

A protein of interest isolated according to the present invention can be verified by using standard techniques such as SDS-PAGE or immunoassays. An SDS-PAGE can be stained with coommassie blue, silver or other suitable agents to visualize the isolated protein. Suitable immunoassays include, but are not limited, Western blots, ELISAs, RIAs, sandwich or immunometric assays, latex or other particle agglutination, or proteomic chips. Protein sequencing and mass spectroscopy can also be used to verify or analyze an isolated protein.

B. UPR Components/Modulators

UPR components/modulators that are amenable to the present invention include molecules that are functional in UPR pathways. They can be naturally occurring or non-naturally occurring. They can be genetically engineered, chemically synthesized, or biologically isolated. A UPR component/modulator can be derived from the same or different species as the host cells. Expression of the UPR component/modulator improves the secretion or ER processing capacity of the host cells. In many cases, co-expression of a UPR component/modulator with a protein of interest in the host cells improves the yield of the protein of interest by at least 2, 3, 4, 5, 10, or more folds.

Examples of UPR components/modulators that are suitable for the present invention include, but are not limited to, transcription factors, such as XBP1 or ATF6. The functional equivalents of these transcription factors, such as fragments of XBP1 or ATF6, can also be used. These fragments retain at least a substantial portion of the transcription activity of the transcriptionally activated XBP1 or ATF6 protein. Downstream effectors of XBP1 or ATF6, such as ER chaperones or enzymes involved in protein glycosylation or vesicle translocation, can also be used.

In addition, non-IRE1 modulators that can activate the expression or biological function of a component of an XBP1- or ATF6-mediated UPR pathway can be used. Such a modulator can modulate the UPR pathway by a mechanism other than self overexpression. For instance, such a modulator can activate the function of a UPR component by directly binding to the component, or modulate the expression of the component by binding to a regulatory sequence in the gene that encodes the component.

Moreover, modulators that can inhibit the expression or biological functions of components of the PERK signaling pathway can be used. These modulators include, without limitation, antibodies, antisense RNA, or RNAi sequences. In addition, dominant negative mutants of the PERK pathway components can be used. An example of such dominant negative mutants is an eIF2a S51A mutant with the replacement of serine at position 51 (murine sequence) to alanine. This substitution eliminates the protein's ability to be phosphorylated and therefore abolishes its inhibitory effect on the protein translation rate during ER stress. Similarly, mutations can be introduced into the kinase domain of PERK to eliminate or reduce its kinase activity to phosphorylate eIF2a, thereby preventing the induction of translational attenuation or apoptosis during ER stress.

In one embodiment, XBP1 protein or a biologically active fragment thereof is employed to increase the yield of a protein of interest in the host cells. XBP1 protein includes two domains commonly found in transcription factors that confer DNA binding and dimerization capability. XBP1 is known as a transcription factor that regulates MHC class II genes by binding to a promoter element referred to as an X box. XBP1 also binds to an enhancer in the T cell leukemia virus type 1 promoter.

Activation of the UPR pathway leads to IRE1-dependent splicing of a small intron from XBP1 mRNA in both *Caenorhabditis elegans* and mammalian model systems. The resulting exons are joined by a tRNA ligase. This splicing event results in a frame-shift in XBP1 mRNA, which produces a protein that has the original N-terminal DNA binding domain but a new C-terminal transactivation domain. In murine cells, the splicing event converts a 267-amino acid XBP1 isoform to a 371-amino acid XBP1 isoform (XBP1s or XBP1p). See Calfon, et al., NATURE, 415: 92-96 (2002).

XBP1p protein binds to the ERSE or UPRE sequences in the promoter regions of many ER chaperone or UPR genes, activating the transcription of these genes. In mammals, at least two ERSE sequences have been identified, ERSE-I and ERSE-II. ERSE-I has a conserved sequence as shown in SEQ ID NO:1 (CCAATNNNNNNNCCACG). ERSE-II has a conserved sequence as depicted in SEQ ID NO:2 (ATTGGNCCACG). In addition, at least two mammalian UPRE sequences have been identified, one having a conserved sequence as depicted in SEQ ID NO:3 (TGACGTGG) and the other having a conserved sequence as illustrated in SEQ ID NO:4 (TGACGTGA).

The XBP1 protein coding sequences can be obtained from a variety of sources. For instance, the coding sequences for human, mouse, rat, chicken, fruit fly, and zebrafish XBP1 proteins can be obtained from the Entrez nucleotide database at National Center for Biotechnology Information (NCBI) (Bethesda, Md.). These sequences have Entrez accession numbers NM_005080, NM_013842, NM_001004210, NM_001006192, NM_079983, or NM_131874, respectively.

A biologically active fragment of an XBP1 protein retains at least a substantial portion of the transcription activation activity of the XBP1p protein. For instance, an XBP1 fragment employed in the invention can retain at least 50%, 60%, 70%, 80%, 90%, or more of the transcription activation activity of XBP1p. Transcriptionally active XBP1 fragments can be selected by numerous means. In one example, a transcriptionally active XBP1 fragment is selected based on its ability to activate the transcription of genes downstream from an ERSE or UPRE sequence.

In another embodiment, ATF6 protein or a biologically active fragment thereof is used to improve the yield of a protein of interest in the host cells. ATF6 is a transmembrane protein which includes a "sensing" domain located in the ER lumen and a cytosolic transcription transactivation domain. Upon ER stress, the cytosolic domain of ATF6 is cleaved off and transported to the nucleus where it binds to the ERSE sequences and thereby activates the downstream UPR genes. At least two ATF6 proteins have been identified—namely, ATF6α and ATF6β. ATF6α and ATF6β are structurally related and share significant similarity in their b-zip domains. Exemplary coding sequences for human mouse, sheep, and chicken ATF6 proteins have Entrez accession numbers NM_007348, XM_129579, AY942654, and XM_422208, respectively.

Similarly to the XBP1 fragments employed in the invention, a biologically active fragment of an ATF6 protein retains at least a substantial portion of the transcription activation activity of the activated ATF6 protein or its cytosolic domain. A biologically active ATF6 fragment can be selected by monitoring its binding to an ERSE sequence and the ability of the fragment to activate the transcription of genes downstream from the ERSE sequence.

In still another embodiment, an ER-resident processing enzyme or chaperone is used to increase the yield of a protein of interest in the host cells. Examples of suitable ER-located enzymes/chaperones include, but are not limited to, GRP78, GRP94, GRP58, the protein disulfide isomerase, calnexin, and calrecticulin. In one example, the endogenous counterpart of an ER enzyme (or chaperone) employed in the present invention has a promoter region including one or more ERSE-I or ERSE-II sequences. In another example, the endogenous counterpart of an ER enzyme (or chaperone) employed in the present invention has a promoter region including one or more UPRE sequences.

The present invention also features the use of a UPR component that is a variant of an endogenous protein. A variant of an endogenous UPR component can be naturally-occurring, such as by allelic variation or polymorphism, or deliberately engineered. The UPR activity of a variant does not decrease substantially compared to the original protein (e.g., an XBP1p, a transcriptionally activated ATF6 protein, or a biologically active fragment thereof). In many embodiments, the variants employed in the present invention retain at least 50% of the UPR activity of the corresponding original proteins. For instance, a variant can retain at least 60%, 70%, 80%, 90%, 95%, 99%, or 100% of the UPR activity of the original protein. In one embodiment, a variant employed in the present invention exhibits an increased UPR activity as compared to the original protein. A desirable variant of a UPR component can be selected such that the expression or activation of the variant enhances the secretion of a co-transfected protein in the host cells.

The amino acid sequence of a variant is substantially identical to that of the original protein. In many instances, the amino acid sequence of a variant has at least 80%, 85%, 90%, 95%, or 99% global sequence identity or similarity to the original protein. Sequence identity or similarity can be determined by a variety of methods. In one embodiment, sequence identity or similarity is determined by using a sequence alignment algorithm. Suitable algorithms for this purpose include, but are not limited to, Basic Local Alignment Tool (BLAST) described in Altschul, et al., J. MOL. BIOL., 215:403-410 (1990), the algorithm of Needleman, et al., J. MOL. BIOL., 48:444-453 (1970), the algorithm of Myers and Miller, COMPUTE. APPLE. BIOSCI., 4:11-17 (1988), and dot matrix analysis. Suitable computer programs for this purpose include, but are not limited to, the BLAST programs provided by NCBI, MegAlign provided by DNASTAR (Madison, Wis.), and the Genetics Computer Group (GCG) GAP program (Needleman-Wench algorithm). For the GAP program, default values may be used (e.g., the penalty for opening a gap in one of the sequences is 11 and for extending the gap is 8). Similar amino acids can be defined by the BLOSSOM substitution matrix.

Numerous methods are available for preparing a desirable variant of a UPR component. For instance, a variant can be derived from the original protein by at least 1, 2, 3, 4, 5, 10, 20, or more amino acid substitutions, deletions, insertions, or other modifications. The substitutions can be conservative or non-conservative. In many instances, conservative amino acid substitutions can be introduced into a protein sequence without significantly changing the structure or biological activity of the protein. Conservative amino acid substitutions can be made on the basis of similarity in polarity, charge, solubility, hydrophobicity, hydrophilicity, or the amphipathic nature of the residues. For instance, conservative amino acid substitutions can be made among amino acids with basic side chains, such as lysine (Lys or K), arginine (Arg or R) and histidine (His or H); amino acids with acidic side chains, such as aspartic acid (Asp or D) and glutamic acid (Glu or E); amino acids with uncharged polar side chains, such as asparagine (Asn or N), glutamine (Gln or Q), serine (Ser or S), threonine (Thr or T), and tyrosine (Tyr or Y); or amino acids with nonpolar side chains, such as alanine (Ala or A), glycine (Gly or G), valine (Val or V), leucine (Leu or L), isoleucine (Ile or I), proline (Pro or P), phenylalanine (Phe or F), methionine (Met or M), tryptophan (Trp or W) or cysteine (Cys or C). Examples of commonly used amino acid substitutions are illustrated in Table 1.

TABLE 1

Example of Amino Acid Substitutions

| Original Residues | Exemplary Substitutions | More Conservative Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

Other desirable amino acid substitutions can also be introduced into a UPR component. For instance, amino acid substitution(s) can be introduced into a UPR component to increase its stability. For another instance, amino acid substitution(s) can be introduced to increase or decrease the UPR activity of a UPR component.

In addition, the present invention features the use of polypeptides that can bind to the UPRE or ERSE sequences of the host cells. These polypeptides, either alone or in combination with other protein(s), can function as transcription factors to activate the transcription of the genes that have the UPRE or ERSE promoter regions.

C. Recombinant Expression Cassettes and Host Cells

A typical recombinant expression cassette employed in the present invention comprises a protein coding sequence operatively linked to a 5' untranslated regulatory region and a 3' untranslated regulatory region. The protein coding sequence can be a genomic sequence, a cDNA sequence, a combination thereof, or other expressible sequences.

In one embodiment, a recombinant expression cassette includes all of the regulatory elements necessary to direct the expression of the encoded protein. Examples of suitable 5' untranslated regulatory elements include promoters, enhancers, or the Kozak sequences. Examples of suitable 3' untranslated regulatory elements include polyadenylation sequences or other transcription/translation termination sequences. Selection of suitable promoters, enhancers, or other regulatory elements for an expression cassette is a matter of routine design within the level of ordinary skill in the art. Many such elements are described in the literature and are available through commercial suppliers.

Promoters suitable for the present invention include constitutive or inducible promoters. These promoters can be endogenous or heterologous to the host cells. In one embodiment, a tissue-specific promoter is used. Suitable tissue-specific promoters include, but are not limited to, liver-specific promoters, lymphoid-specific promoters, T cell-specific promoters, neuron-specific promoters, pancreas-specific promoters, or mammary gland-specific promoters. A developmentally-regulated promoter can also be used. A recombinant expression cassette having a tissue-specific or developmental-regulated promoter can be used to prepare transgenic animals or plants. Protein(s) encoded by such a recombinant expression cassette can be produced in specific tissue(s) or at specific developmental stage(s) of the transgenic animals or plants.

In another embodiment, an inducible expression system is used to produce a protein of interest or a UPR component/modulator. Systems suitable for this purpose include, but are not limited to, the Tet-on/off system, the Ecdysone system, and the Rapamycin system. The Tet-on/off system is based on two regulatory elements derived from the tetracycline-resistance operon of the *E. coli* Tn10 transposon. The system includes two components, a regulator cassette and a reporter cassette. In one format of the Tet-off system, the regulator cassette encodes a hybrid protein comprising a Tet repressor (tetR) fused to the VP16 activation domain of herpes simplex virus (HSV). The reporter cassette includes a tet-responsive element (TRE) operatively linked to a report gene. The reporter gene can encode, for example, a protein of interest or a UPR component/modulator. In the absence of inducer (e.g., tetracycline or doxycycline), the tetR-VP16 fusion protein binds to the TRE, thereby activating the transcription of the reporter gene. In one format of the Tet-on system, the regulator cassette encodes a hybrid protein comprising a mutated Tet repressor (rtetR) fused to the VP16 activation domain of HSV. The rtetR is a reverse Tet repressor which binds to and activates the TRE in the presence of inducer (e.g., tetracycline or doxycycline).

The Ecdysone system is based on the molting induction system in *Drosophila*. In one format, the system includes a regulator cassette which encodes a functional ecdysone receptor, and a reporter cassette which includes an ecdysone-responsive promoter operatively linked to a reporter gene. In the presence of an inducer (such as ponasterone A or muristerone A), the ecdysone receptor binds to the ecdysone-responsive promoter, activating the transcription of the reporter gene.

The Rapamycin system, also known as the CID system ("chemical inducers of dimerization"), employs two chimeric proteins. The first chimeric protein includes FKBP12 fused to a DNA-binding domain that binds to a DNA response element. The second chimeric protein includes FRAP fused to a transcriptional activation domain. The addition of rapamycin causes dimerization of the two chimeric proteins, thereby activating the expression of genes controlled by the DNA response element.

In one example, a recombinant expression cassette employed in the present invention comprises SEQ ID NO:5. Transcription of SEQ ID NO:5 produces a non-spliced human XBP1 mRNA. ER stress activates IRE1, which cleaves an intron from the non-spliced mRNA. Translation of the spliced mRNA produces a mature and functional XBP1 protein, the amino acid sequence of which is depicted in SEQ ID NO:6.

In another example, a recombinant expression cassette employed in the present invention comprises SEQ ID NO:7. SEQ ID NO:7 does not include any cleavable intron sequences. Expression of SEQ ID NO:7 produces a mature and functional human XBP1 protein (SEQ ID NO:6). Other nucleic acid sequences that encode SEQ ID NO:6 or a functional equivalent thereof can also be used to prepare a recombinant expression cassette of the invention. These nucleic acid sequences may or may not include introns or other removable sequences.

In still another example, a recombinant expression cassette employed in the present invention comprises SEQ ID NO:8. Transcription and translation of SEQ ID NO:8 produce a human ATF6 protein, the amino acid sequence of which is illustrated in SEQ ID NO:9.

In a further example, a recombinant expression cassette employed in the present invention comprises a nucleic acid sequence encoding amino acid residues 1-366 of SEQ ID NO:9. An example of such a nucleic acid sequence is nucleotides 1-1098 of SEQ ID NO:8. Amino acid residues 1-366 of SEQ ID NO:9 include the entire basic region and the majority of the leucine zipper region of the human ATF6 protein. This ATF6 fragment has been shown to be capable of activating endogenous GRP78 genes. See Haze, et al., MOL. BIOL. CELL, 10:3787-3799 (1999).

Recombinant cassettes encoding XBP1 or ATF6 proteins derived from non-human species can also be used in the present invention. For instance, XBP1 or ATF6 proteins of rodent or other animal species can be used. These XBP1 or ATF6 proteins can be selected such that co-expression of these proteins with a protein of interest improves the yield of the latter protein in the host cells.

A recombinant expression cassette can be incorporated into host cells by a variety of means. In one embodiment, a recombinant expression cassette is introduced into a eukaryotic host cell by using a transfection or transduction vector. Vectors suitable for this purpose include, but are not limited to, insect cell expression vectors (e.g., baculovirus expression vectors) or mammalian expression vectors. These vectors can be derived from a variety of sources, such as episomes, cosmids, viruses, or combinations thereof. In many cases, these vectors include selectable markers to facilitate their incorporation into the host cells.

In another embodiment, a recombinant expression cassette employed in the present invention is constructed by modifying an endogenous gene in the host cells. The endogenous gene can encode a protein of interest or a UPR component/modulator. Many portions in the endogenous gene can be modified to achieve a desired expression or regulation effect. For instance, the original promoter of an endogenous gene can be replaced by a viral promoter to increase the expression level of the gene.

A recombinant expression cassette can be incorporated into a host cell in various forms. For instance, a recombinant expression cassette can be integrated into a chromosome or the genome of a host cell. A recombinant expression cassette can also be carried by a non-integrated expression vector in a host cell. Methods for stably or transiently introducing an expression vector or cassette into a host cell are known in the art. In one example, the expression vector or cassette is incorporated into a chromosome of the host cell by targeted integration. Methods suitable for this purpose include, but are not limited to, the Cre-lox recombination system and those described in U.S. Pat. Nos. 6,656,727, 6,537,542 and 6,541,231.

In many embodiments, a genetically-engineered cell of the present invention includes (1) a first recombinant expression cassette encoding a protein of interest and (2) a second recombinant expression cassette encoding a UPR component/modulator (e.g., XBP1 or ATF6). The ratio of the total number of the first recombinant expression cassette over the total number of the second recombinant expression cassette in the cell can range, for example, from no more than 0.1:1 to at least 10:1. Non-limiting examples of suitable ratios include from 0.2:1 to 5:1, from 0.5:1 to 5:1, from 1:1 to 2:1, from 1:1 to 3:1, from 1:1 to 4:1, from 1:1 to 5:1, from 2:1 to 3:1, from 2:1 to 4:1, and from 2:1 to 5:1. The first and the second recombinant expression cassettes can be carried by the same or different vectors and driven by the same or different promoters which have the same or different strengths. In one example, the promoter in the first recombinant expression cassette has the same or similar strength as that in the second recombinant expression cassette, and the ratio of the total number of the first recombinant cassette to the total number of the second recombinant cassette in the cell is at least 1:1, 2:1, 3:1, 4:1, 5:1, or more.

Host cells suitable for the present invention include animal or plant cells. The host cells can be cultured cells, such as cell lines or primary cultures. They can also be cells in transgenic animals or plants. The selection of suitable host cells and methods for culture, transfection/transduction, amplification, screening, product production, and purification are known in the art.

In one embodiment, the host cells employed in the present invention are mammalian cells. Examples of suitable mammalian cells include, but are not limited to, Chinese hamster ovary (CHO) cells, HeLa cells, COS cells, 293 cells, CV-1 cells, and other mammalian cell lines collected by American Type Culture Collection (Manassas, Va.). In certain cases, it is desirable to produce therapeutic or prophylactic proteins in human cells, which often provide desired post-translational modifications on the expressed proteins.

The host cells employed in the present invention can also be hybrid cells created through fusion of two or more cells. In many cases, a hybrid cell employed in the present invention is generated by fusing an animal cell (e.g., a mammalian cell) and a cancer/immortal cell (e.g., a myeloma or blastoma cell). The animal cell and the cancer/immortal cell can be derived from the same species. They can also be derived from different species. Any method known in the art may be used to produce hybrid cells. These methods include, but are not limited to, electrofusion or chemical fusion (e.g., polyethylene glycol fusion).

A recombinant expression cassette can be introduced or incorporated into a hybrid cell before or after the fusion event. For instance, a recombinant expression cassette encoding a protein of interest can be incorporated into a mammalian cell before the cell is fused with a cancer cell expressing an exogenous UPR component or modulator. For another instance, a mammalian cell can be first transfected or transduced with recombinant expression vector(s) that encodes a protein of interest and a UPR component or modulator, and then fused with a cancer cell. Other procedures can also be used to prepare hybrid cells of the present invention.

In many embodiments, the cancer/immortal cells used for preparing hybrid cells are sensitive to one or more selective agents. For instance, the cancer/immortal cells can be sensitive to a culture medium containing hypoxanthine, aminopterin and thymidine, which is known as "HAT medium." These HAT-sensitive cells are fused to cells insensitive to HAT medium. Hybrid cells thus produced are selected against HAT, which kills unfused cells. The fused cells are then screened for desired features.

The present invention also features animals or plants that comprise a eukaryotic host cell of the present invention. Methods for incorporating a recombinant cell into an animal or a plant are well known in the art. In many embodiments, the animals or plants are transgenic animals or plants which include one or more transgenes that encode a protein of interest and a UPR component/modulator. Transgenic animals or plants can be prepared by using standard techniques. In one embodiment, the transgenic animals are non-human animals.

The present invention further features animal or plant cell cultures that are transfected or transduced with one or more expression vectors encoding (1) a protein of interest and (2) a UPR component/modulator. The cell cultures can be mammalian cell cultures, insect cell cultures, plant cell cultures, or other cultures suitable for the production of proteins of interest. The expression vector(s) can be transfected or transduced transiently or stably. In one embodiment, the expression vector(s) employed comprises a first recombinant expression cassette encoding a protein of interest and a second recombinant expression cassette encoding a UPR component/modulator (e.g., XBP1 or ATF6). The first and the second expression cassettes can be carried by the same or different vectors. They can be driven by the same or different promoters. The molar ratio of the first recombinant expression cassette over the second recombinant expression cassette can range, for example, from no more than 0.1:1 to at least 10:1.

In one example, the promoter employed by the first recombinant cassette has the same or similar strength as the promoter employed by the second recombinant cassette, and the molar ratio of the first recombinant cassette over the second recombinant cassette in the cell culture ranges from 0.5:1 to 10:1, such as at least 1:1, 2:1. 3:1, 4:1, 5:1, or more.

D. Pharmaceutical Compositions

A therapeutic or prophylactic protein produced by the present invention can be used to prepare a pharmaceutical composition for the treatment of a patient or animal in need thereof. A pharmaceutical composition of the present invention typically includes an effective amount of a therapeutic or prophylactic protein and a pharmaceutically acceptable carrier. Suitable pharmaceutically acceptable carriers include solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, that are compatible with pharmaceutical administration. The use of such media and agents for pharmaceutically active substances is well-known in the art. Supplementary agents can also be incorporated into the composition.

A pharmaceutical composition of the present invention can be formulated to be compatible with its intended route of administration. Examples of routes of administration include parenteral, intravenous, intradermal, subcutaneous, oral, inhalative, transdermal, rectal, transmucosal, topical, and systemic administration. In one example, the administration is carried out by an implant.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

A pharmaceutical composition of the present invention can be administered to a patient or animal in a desired dosage. A suitable dosage may range, for example, from 5 mg to 100 mg, from 15 mg to 85 mg, from 30 mg to 70 mg, or from 40 mg to 60 mg. Dosages below 5 mg or above 100 mg can also be used. The pharmaceutical composition can be administered in one dose or multiple doses. The doses can be administered at intervals such as once daily, once weekly, or once monthly.

Toxicity and therapeutic efficacy of a therapeutic protein can be determined by standard pharmaceutical procedures in cell culture or experimental animal models. For instance, the $LD_{50}$ (the dose lethal to 50% of the population) and the $ED_{50}$ (the dose therapeutically effective in 50% of the population) can be determined. The dose ratio between toxic and therapeutic effects is the therapeutic index, and can be expressed as the ratio $LD_{50}/ED_{50}$. In many cases, therapeutic proteins that exhibit large therapeutic indices are selected.

The data obtained from cell culture assays and animal studies can be used to formulate a range of dosages for use in humans. In one embodiment, the dosage lies within a range that exhibits therapeutic effectiveness in at least 50% of the population with little or no toxicity. The dosage may vary within this range depending upon the dosage form employed and the route of administration utilized.

The dosage regimen for the administration of a therapeutic protein produced by the present invention can be determined by the attending physician based on various factors such as the action of the protein, the site of pathology, the severity of disease, the patient's age, sex and diet, the severity of any inflammation, time of administration, and other clinical factors. In one example, systemic or injectable administration is initiated at a dose which is minimally effective, and the dose is increased over a pre-selected time course until a positive effect is observed. Subsequently, incremental increases in dosage are made limiting to levels that produce a corresponding increase in effect while taking into account any adverse affects that may appear.

Progress of a treatment can be monitored by periodic assessment of disease progression. The progress can be monitored, for example, by X-rays, MRI or other imaging modalities, synovial fluid analysis, or clinical examination.

A therapeutic or prophylactic protein of interest can also be introduced into a human or animal by using a gene delivery vector. Vectors suitable for this purpose include, but are not limited to, viral vectors such as retroviral, lentiviral, adenoviral, adeno-associated viral (AAV), herpes viral, alphavirus, astrovirus, coronavirus, orthomyxovirus, papovavirus, paramyxovirus, parvovirus, picomavirus, poxvirus, or togavirus vectors. Liposomally-encapsulated expression vectors can also be used for gene delivery. In many embodiments, the gene delivery vector encodes both the protein of interest and a UPR modulator. Co-expression of the UPR modulator enhances the production of the protein of interest in the target cells (e.g., tumor cells or other dysfunctional cells). The protein of interest and the UPR modulator can also be delivered to the target cells by using different vectors. Gene delivery can be conducted in vivo or ex vivo.

In one embodiment, cell-specific gene delivery methods are employed for introducing a therapeutic/prophylactic protein of interest or a UPR modulator into the target cells. Many cell-specific gene delivery methods known in the art can be used for the present invention. For instance, a cell-specific ligand (e.g., an antibody specific to a surface antigen of the target cell) can be incorporated or conjugated to the envelope of a viral vector which encodes a therapeutic/prophylactic protein or a UPR modulator. This ligand can mediate entry of the viral vector into a specific cell type. Antibody-conjugated liposomes can also be used for delivering gene therapy vectors to specific target cells.

It should be understood that the above-described embodiments and the following examples are given by way of illustration, not limitation. Various changes and modifications within the scope of the present invention will become apparent to those skilled in the art from the present description.

E. Examples

Example 1

COS-1 and DUKX Cell Lines

COS-1 cells were obtained from American Type Culture Collection (ATCC), Manassas, Va., with ATCC number CRL-1650. CHO DUKX cells and PA DUKX cells were both derived from CHO-K1 (ATCC number CCL-61), which is a derivative of the Chinese hamster ovary (CHO) cells.

The CHO DUXK cells, which are also referred to as DUXK B11 or DXB11 cells, are deficient in production of dihydrofolate reductase (dhfr), a critical enzyme in the process of DNA replication. To select cells in which both dhfr alleles were mutated, Urlaub and Chasin, PROC. NATL. ACAD. SCI. U.S.A., 77:4216-4220 (1980), performed the mutagenesis and selection in two steps. The selective agent used against dhfr+ cells was tritiated deoxyuridine. Tritiated deoxyuridine is toxic to cells due to its incorporation into DNA and subsequent radioactive decay. Incorporation of deoxyuridine into DNA requires its conversion to thymidilic acid, a process for which DHFR is essential. dhfr− mutant cells are unable to incorporate deoxyuridine into their DNA and thus are able to survive in the presence of tritiated deoxyuridine. Some dhfr+ cells as well as mutants deficient in some other enzyme necessary for the incorporation of deoxyuridine into DNA, may survive also. dhfr− mutants may be distinguished because they are unable to conduct de novo biosynthesis of glycine, hypoxanthine, and thymidine; thus they require exogenous nucleosides for growth.

In the first step of selection as used by Urlaub and Chasin, supra, wild-type cells were subjected to ethyl methane sulfonate (EMS) mutagenesis and selected with tritiated deoxyuridine in the presence of dhfr-inhibiting methotrexate (MTX) to isolate a presumptive heterozygote (d+/d−). By using a concentration of MTX that was sufficient to inactivate all the DHFR in the heterozygote (d+/d−), but not in the homozygote (d+/d+), the homozygote had residual DHFR activity and incorporated tritiated deoxyuridine. By virtue of this incorporation, (the d+/d+) cells were selected against and only the heterozygotes were able to survive. After three rounds of selection, pooling, and expansion of the surviving cells, the presumptive heterozygote cell line, UKB25 was isolated. UKB25 cells were further mutagenized with gamma-irradiation and selected in tritiated deoxyuridine in the absence of MTX. The surviving colonies exhibited triple auxotrophy for glycine, hypoxanthine, and thymidine, which indicated a dhfr−phenotype. Colonies exhibiting this triple auxotrophy were cloned and shown to be deficient in dhfr activity. Analysis of one such clone by Southern Blot hybridization revealed that the dhfr genes did not undergo any gross rearrangements. This clone was designated DXB11.

The DXB11 cells thus generated were examined to confirm the predicted characteristics of the cell line. The DUKX B11 cells were found to be genotypically similar to the CHO-K1 cell line from which they were derived. They are hypodiploid CHO cells, with 20 chromosomes that have been extensively studied cytogenetically. Geimsa banding of metaphase DUKX B11 chromosomes demonstrated that the DUKX B11 cells are CHO-K1 derivatives. The DUKX B11 cells are DHFR-deficient and therefore auxotrophic for glycine, purine nucleosides, and thymidine. This DHFR-deficient phenotype of the DUKX B11 cells is the basis of the genetic selection used for the transfer of recombinant heterologous protein expression plasmids into the cells.

In some experiments, the medium used for culturing DUKX B11 cells did not contain hypoxanthine or thymidine. Without dihydrofolate reductase activity, the only means for cells to survive and replicate was by the supplementation of nucleosides in the growth medium to compensate for the cells inability to make them. Therefore, adenosine, deoxyadenosine, and thymidine were added to the growth medium for DUKX B11 cells. These were each added at a concentration of 10 μg/ml. This concentration was in excess of what the cells required under routine small-scale growth conditions.

DUKX B11 cells are useful for introducing expression plasmids containing cDNAs for desired proteins. Because they lack endogenous DHFR activity it can be used as a selectable and amplifiable marker when generating cell lines to produce heterologous proteins. By either co-transfecting another expression vector containing a cDNA for dhfr, or by putting the dhfr cDNA in close proximity to the cDNA of interest on the same expression vector, one can use dhfr activity as a marker for which cells have taken up the expression plasmid containing the desired gene, and are likely to produce the desired protein. By withholding exogenous nucleosides after transfection, only cells that incorporate a vector containing the dhfr gene will be able to produce dhfr and thereby survive. The survived cells can now produce the desired protein. This may be accomplished by virtue of a bicistronic message when the desired cDNA and the dhfr are on the same plasmid, or by individual messages when the genes are on different plasmids, which usually co localize on the chromosome during a transfection event. When using two separate plasmids, altering the ratio of dhfr-containing plasmid to cDNA-containing plasmid can enhance one's ability to select cells that contain both.

The DUKX B11 cells are dhfr-deficient by virtue of a point mutation in the dhfr gene and therefore reversion to a dhfr+ phenotype is possible. This reversion and ability to grow without exogenous nucleosides was observed during a serum-free suspension adaptation effort. The population of DUKX cells in culture remained dhfr− for approximately 154 cumulative population doublings (CPD) from the initiation of a suspension culture. However, when the population was checked again for dependence on exogenous nucleosides at 190 CPD, a phenotypic reversion was evident. Coincident with the dhfr+ phenotype is a significant increase in the average growth rate of these cells. Because the dhfr− phenotype is desirable for transfection and gene amplification strategies, a serum-free suspension of adapted DUKX cells was made after 153.8 CPD. Because these cells were adapted to growth in serum-free suspension culture prior to an expression vector being introduced, they are called "pre-adapted", and are referred to as "PA DUKX."

Non-adapted, FBS-dependent DUKX monolayers can be used for transfecting expression vectors. Once the expression of a heterologous gene and dhfr are achieved, each new cell line can be adapted to FBS-free suspension growth. The adaptation period after transfection using monolayer cells is often lengthy. "Pre-adapted" DUKX cells can be also used as host cells for transfection. These PA DUKX cells often offer advantages from a time and effort perspective as the period of re-adaptation to serum free suspension growth post-transfection is usually shorter. See Sinacore, et al., BIOTECHNOLOGY AND BIOENGINEERING, 52:518-528 (1996).

Example 2

Induction of ER Stress by Overexpression of BMP6 in PA DUKX Cells pSMED2/XBP1 and pSMED2/BMP6 (+) or empty pSMED2 vector (−) were cotransfected into PA DUKX cells. pSMED2/XBP1 and pSMED2/BMP6 expression vectors encode XBP1 and BMP6, respectively. Both vectors are driven by a CMV promoter. Transfections were carried out in 6-well plates using Fugene6 (Roche, Indianapolis, Ind.). The growth medium for the cells was Alpha media (Gibco) supplemented with nucleosides and 10% FBS (heat inactivated and dialyzed) and Penicillin/Streptomycin/Glutamine (Gibco).

Cells were lysed in Cell Lysis Buffer (Cell Signaling Technology, Beverly, Mass.) with the addition of 400 mM NaCl and 1 Complete Mini (a protease inhibitor cocktail tablet from Roche, Indianapolis, Ind.). Lysates were taken at 7, 24, 31, and 48 h after transfection and run on a 10% tricine gel, followed by Western blot analysis (FIG. 1). The Western blot analysis was performed by using a blocking buffer of 4% non-fat dry milk, 1% BSA and 0.1% Tween20 in TBS, and a wash buffer of 0.1% Tween20 in TBS. Antibodies were diluted in the blocking buffer. Titration for Western was 1:1000 anti-XBP1 (Santa Cruz Biotechnology) followed by 1:5000 goat anti-rabbit antibody conjugated with horseradish peroxidase (The Jackson Laboratory). FIG. 1 indicates that overexpression of BMP6 in PA DUKX cells caused ER stress, as measured by the increase of XBP1p protein (about 54 kD).

Example 3

Figure 2:
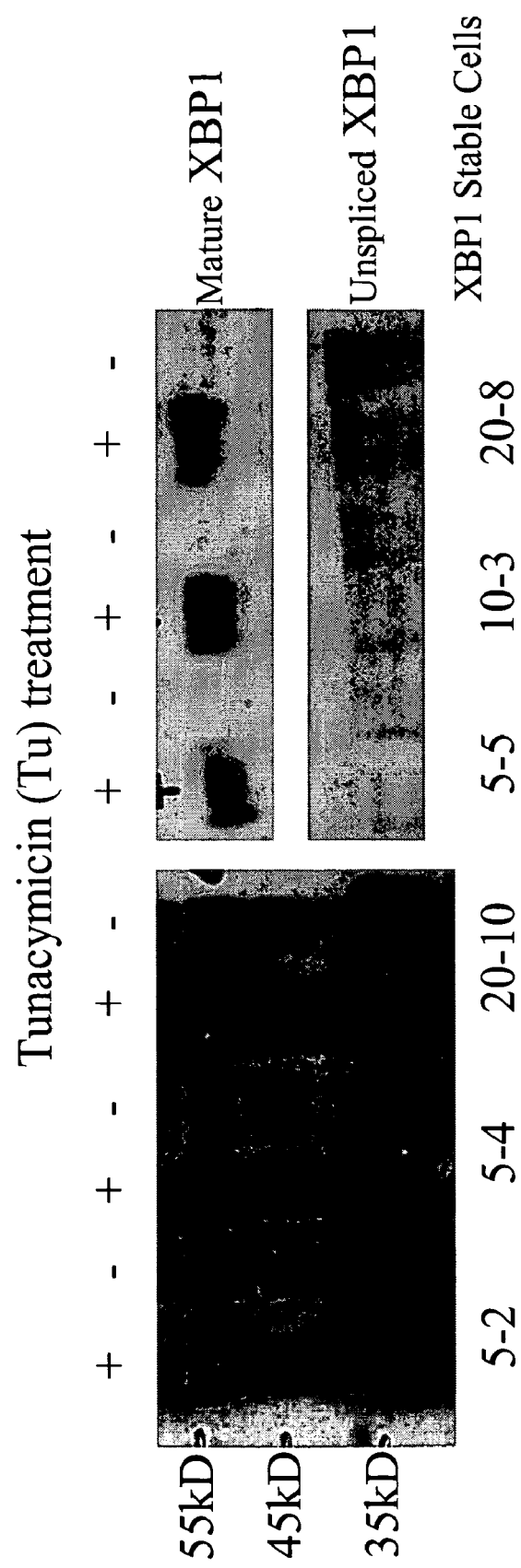
FIG. 2 indicates expression of exogenous XBP1 in stably transfected cell lines under unstressed or stressed conditions.
Figure 3:
FIG. 3 shows increased secretion of BMP6 in several XBP1 cell lines than in parental CHO DUKX cells.
Figure 4:
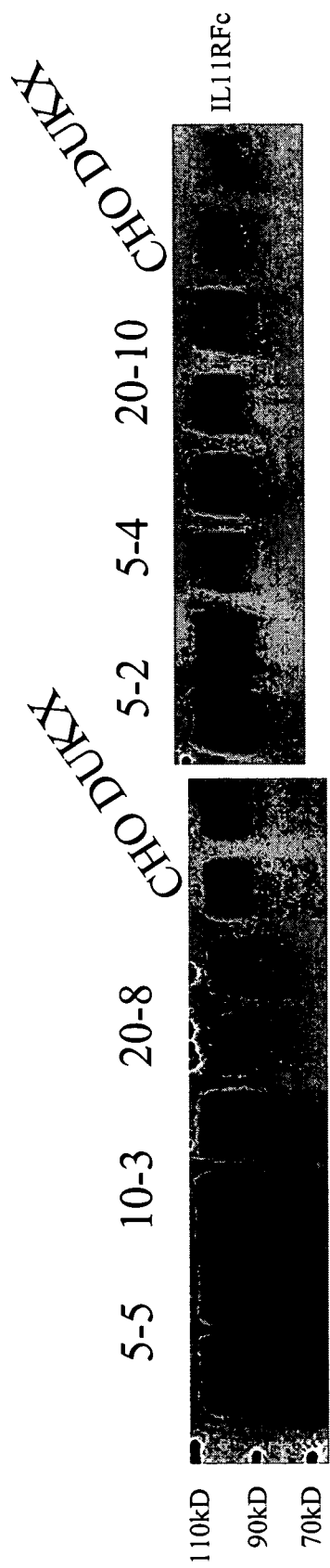
FIG. 4 illustrates increased secretion of IL11RFc in several XBP1 cell lines than in parental CHO DUKX cells.

Cell Lines Stably Transfected with XBP1 pSMED2/XBP1 vector was transfected into CHO DUKX cells to create stable cell lines. DFHR gene on the pSMED2 vector allows for methotrexate (MTX) resistance. Transfected cells were plated in 5, 10, or 20 nM MTX concentrations. Three 5 nM MTX colonies (5-2, 5-4, 5-5), one 10 nM colony (10-3), and one 20 nM colony (20-10) were isolated. Cells from each colony were treated with (+) or without (−) tunacymicin (Tu), a chemical known to cause ER stress. Lysates were run on a 10% tricine gel, followed by Western blot analysis (FIG. 2) using rabbit polyclonal anti-XBP1 antibody (Santa Cruz Biotechnology). FIG. 2 demonstrates that more mature XBP1 was produced in XBP1 stable cell lines when the cells were stressed by Tu treatment.

pSMED2/BMP6 was transiently transfected into XBP1 stable (5-2,5-4, and 20-10) and parental (CHO DUKX) cell lines. Conditioned media collected 48 h after transfection were run on a 10% tricine gel, followed by Western blot analysis. The Western blot membrane (FIG. 3) was probed with a mouse monoclonal anti-BMP5 antibody (1:2000) which strongly crossreacts with BMP6. The secondary antibody was goat anti-mouse antibody conjugated with horseradish peroxidase (1:5000) (The Jackson Laboratory). Each lane in FIG. 3 represents a separate experiment for a respective cell line. As demonstrated in FIG. 3, more BMP6 was secreted in XBP1 stable cell lines selected with 5 nM and 10 nM MTX than in parental cells.

pSMED2/IL11RFc, which encodes an IL11RFc protein, was also transiently transfected into XBP1 stable and parental cell lines. Conditioned media collected 48 h after transfection were run on a 10% tricine gel, followed by Western blot analysis. The Western blot membranes (FIG. 4) were probed with goat anti-human Fc antibody conjugated with horseradish peroxidase (The Jackson Laboratory). More IL11 RFc was secreted in the majority of XBP1 cell lines selected with 5 nM MTX than in CHO DUKX cells.

Example 4

Figure 5:
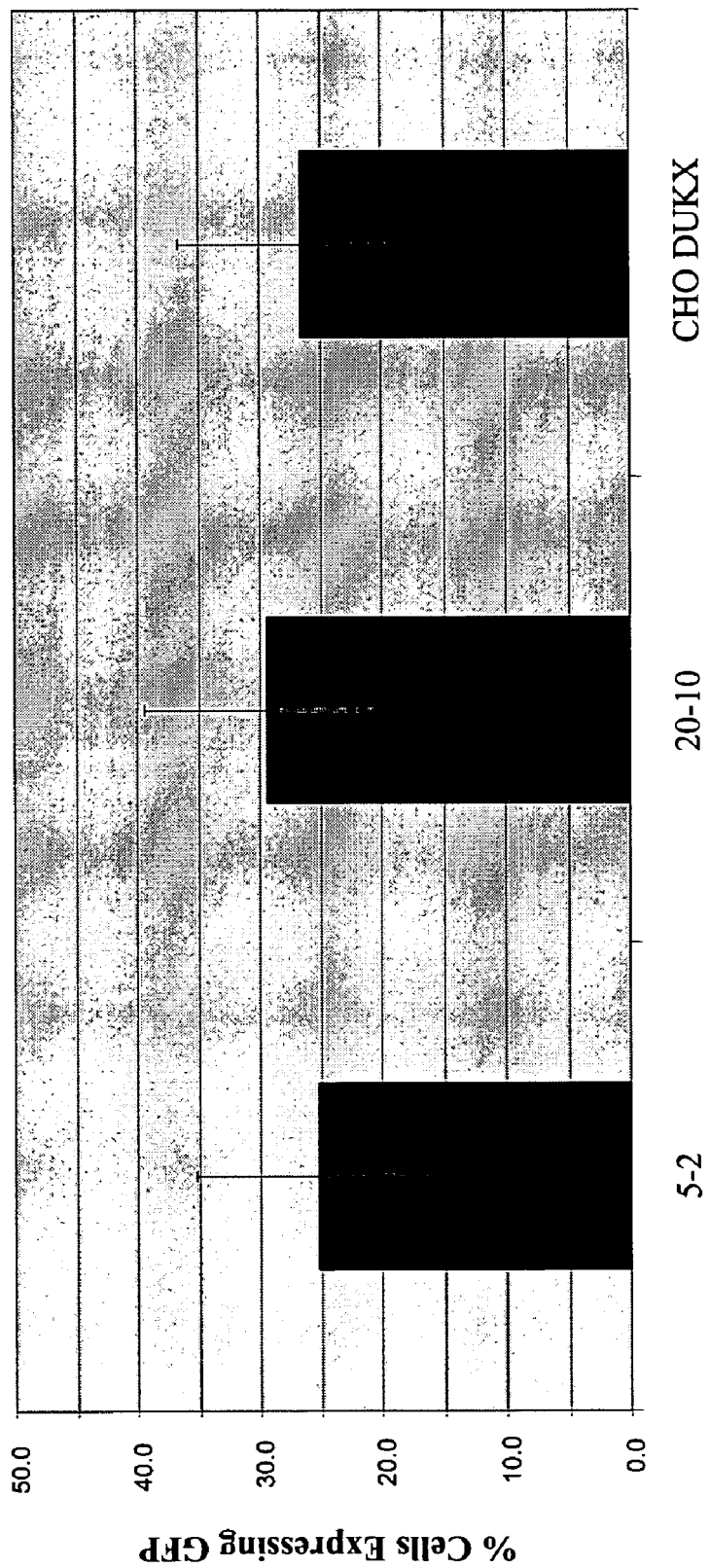
FIG. 5 demonstrates that the transfection efficiency of GFP is similar in selected XBP1 and parental CHO DUKX cell lines.

Comparison of Transfection, Transcriptional and Translational Efficiencies Among XBP1 Stable Cell Lines and their Parental CHO Cells 5-2, 20-10 and CHO DUKX cells were counted and equal amounts were transiently transfected with a construct encoding green fluorescent protein (GFP). Cells were visualized at 10×10 magnification and transfection efficiency (% Cells Expressing GFP) was determined by comparing GFP fluorescent cells to total cells in three visual fields per cell line. The comparison result indicates that the transfection efficiency of GFP is similar in all XBP1 and CHO DUKX cell lines tested (FIG. 5).

Figure 6:
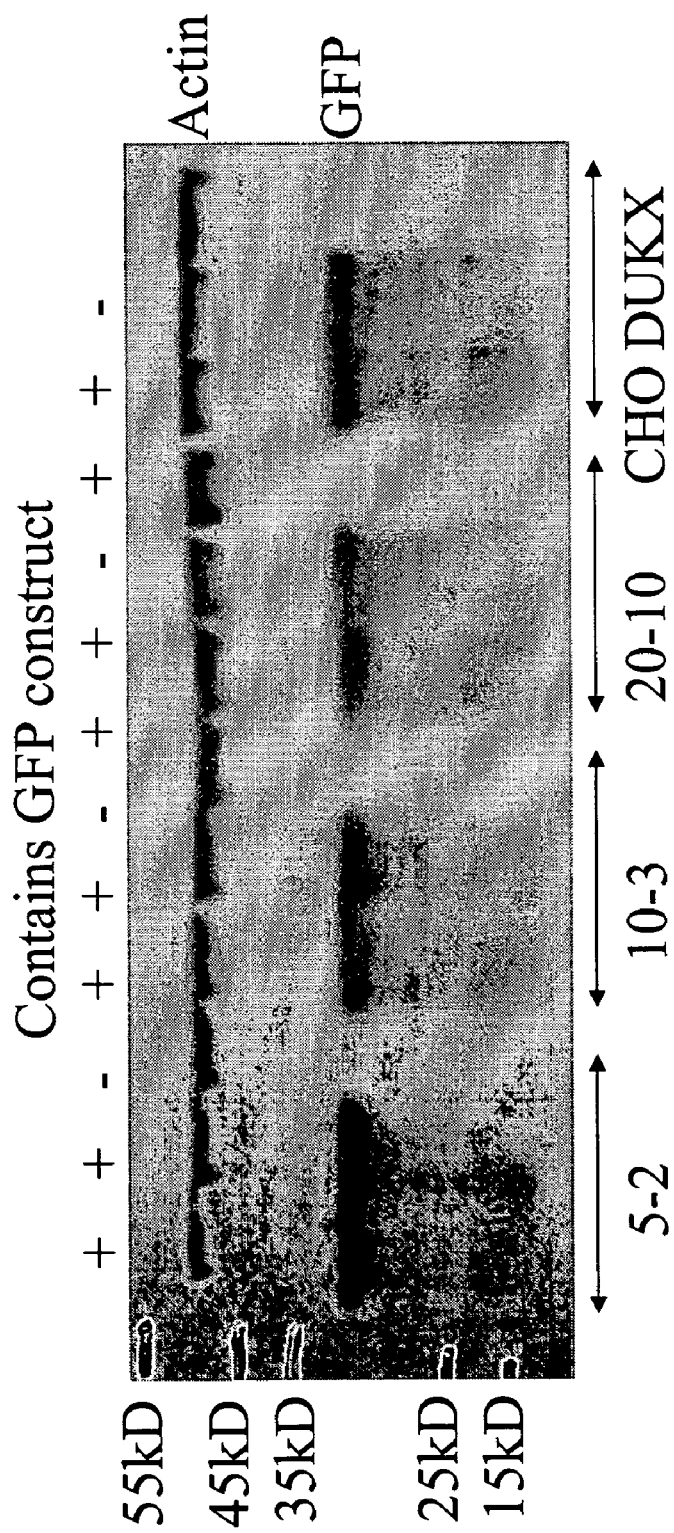
FIG. 6 shows that the transcriptional and translational efficiency of GFP is similar in selected XBP1 and parental CHO CUKX cell lines.

In a further experiment, constructs encoding (+) or not encoding (−) GFP were transiently transfected into XBP1 stable and parental cell lines. Cell lysate collected 48 h after transfection was run on a 10% tricine gel, followed by Western blot analysis (FIG. 6). Each lane in FIG. 6 represents a separate experiment. The Western blot membrane was probed with rabbit polyclonal anti-GFP antibody and mouse monoclonal anti-actin antibody for loading control. As demonstrated by FIG. 6, the sum of transcriptional and translational efficiencies for GFP is similar in all cell lines investigated.

Example 5

Cell Transiently Transfected with ATF6

Figure 7:
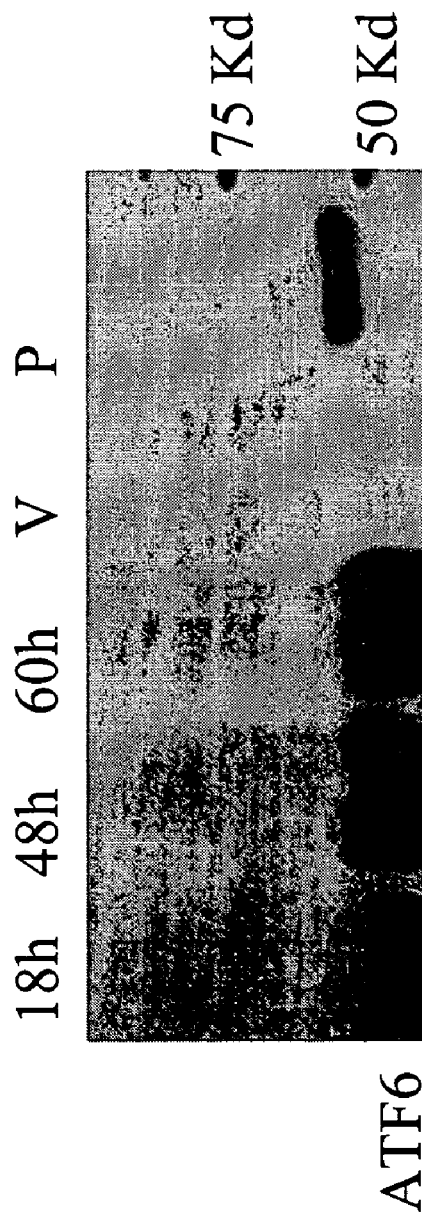
FIG. 7 illustrates the successful expression of inducible ATF6 protein in COS-1 cells.

Flag-tagged cDNA from the active soluble domain of ATF6 was cloned into a Tet/off inducible expression vector ptTATOP6 and transiently transfected into COS-1 cells. The ptTATOP6 vector includes an inducible promoter which controls the expression of the fusion protein comprising ATF6 and the Flag tag. Cells lysate collected at 18, 48 and 60 h after transfection was run on a 10% tricine gel, followed by Western blot analysis. The Western blot membrane (FIG. 7) was probed with anti-flag antibody. "V" indicates an empty ptTATOP6 vector, and "P" represents a flag positive control. As illustrated by FIG. 7, ATF6 protein was successfully expressed in COS-1 cells in the absence of doxycycline.

Example 6

Co-Expressing Target Genes with XBP1 or ATF6 in Proper Ratios Enhances the Secretion of the Target Genes in HEK293 Cells HEK293-FT and HEK293-EBNA were grown and maintained in a humidified incubator with 5% $CO_2$ at 37° C. in free-style 293 media (Invitrogen, Carlsbad, Calif.) supplemented with 5% fetal bovine serum.

Transient expression was performed in 50-ml spinners or 24-well plates, or 1L spinners. For the culture volume of 50 ml (or 1 L), 25 μg (or 0.5 mg for 1 L) of plasmid DNA was mixed with 400 μg (8 mg for 1L) of Polyethylenimine (PEI, 25 kDa, linear, neutralized to pH7.0 by HCl, 1 mg/ml, Polysciences, Warrington, Pa.) in 2.5 ml (50 ml for 1 L) of serum-free 293 media. The spinners were incubated at 37° C. with a rotation rate of 170 rpm on a P2005 Stirrer (Bellco) for 72-144 hours before harvest. For a 24-well plate format, 1 g of DNA was mixed with 8 μg of PEI in 0.5 ml of serum-free 293 media. Then the mixtures were mixed with 0.5 ml of HEK293 cells in 293 media with 10% FBS at the cell density of $0.5 \times 10^6$ cells/ml. The plates were incubated at 37° C. on an Orbital shaker (BellCo) with a rotation rate of 300 rpm for 72 hours before harvest.

pSMED2 and pSMEDA were used for the DNA construction. C-terminal His6-tagged secreted frizzled-related protein 1 (sFRP-1), and C-terminal Flag-tagged aggrecanase-2 (Agg-2) were subcloned into pSMEDA. C-terminal His6-tagged neurotrophic tyrosine kinase, receptor, type 2 (TrkB) was subcloned into pSMED2. These subcloned genes did not have any transmembrane or cytoplasmic domains, thereby allowing secretion of the expressed products.

C-terminal His6-tagged Prop1 and Prop34-LBD were subcloned into pcDNA3.1 (Invitrogen, Carlsbad, Calif.). Prop1 and Prop34-LBD were derived from low density lipoprotein receptor-related protein 5 (LRP5) with deletion of the transmembrane and cytoplasmic domains. The amino acid sequences of Prop1 and Prop34-LBD are depicted in SEQ ID NOs:10 and 11, respectively. SEQ ID NO:10 includes a His6 tag at amino acids 342-347 and a Flag tag at amino acids 348-356. SEQ ID NO:11 includes a His6 tag at amino acids 795-800 and a V5 tag at amino acids 778-794.

1 μg of Prop1-his6-Flag in pcDNA3.1 was co-transfected with 0.3 μg (1:3) or 1 μg (1:1) of XBP1p in pSMED2 vector into HEK293T cells. Both pcDNA3.1 and pSMED2 are driven by a CMV promoter. Conditioned media were harvested at 72 hr after DNA transfection. Samples were separated by SDS-PAGE and immunoblotted with anti-His4 antibodies. Duplicates experiments (Set#1 and Set#2) were performed. As demonstrated in FIG. 8A, co-transfection of XBP1 with Prop1 in the ratios of 1:1 or 1:3 drastically improved the expression of Prop1.

Figure 8:
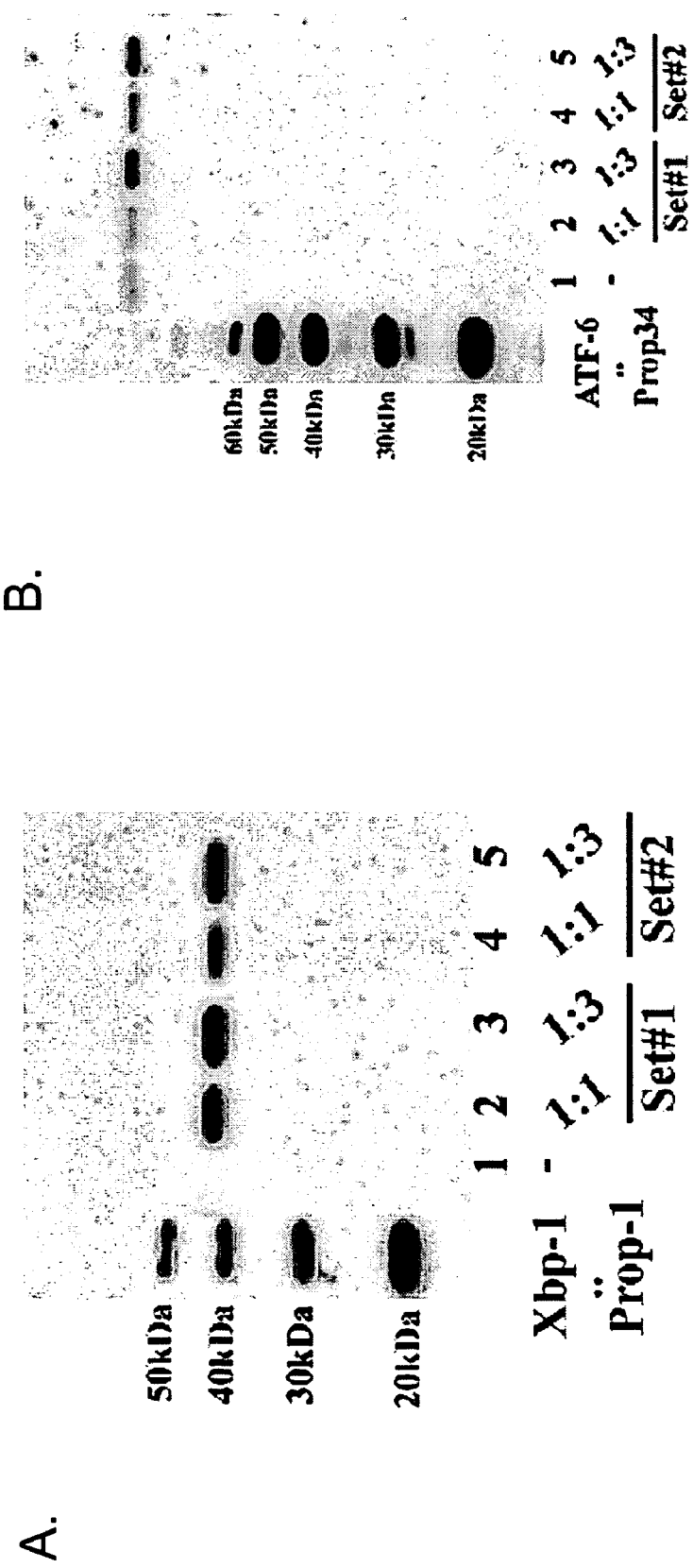
FIG. 8 depicts the effects of XBP1 or ATF6 in different ratios with target protein cDNAs on the production of target proteins.

In another experiment, 1 μg of Prop34-LBD-V5-his6 in pcDNA3.1 was co-transfected with 0.3 μg (1:3) or 1 μg (1:1) of ATF6 in ptTATOP6 vector into HEK293T cells. Like pSMED2, ptTATOP6 is also driven by a CMV promoter. Conditioned media harvested at 72 hr after DNA transfection were analyzed by SDS-PAGE and immunoblotting with anti-His4 antibody. FIG. 8B shows that co-transfection of ATF6 with Prop34-LBD-V5-his6 in the ratio of 1:1 or 1:3 significantly enhanced the expression of Prop34-LBD.

Figure 9:
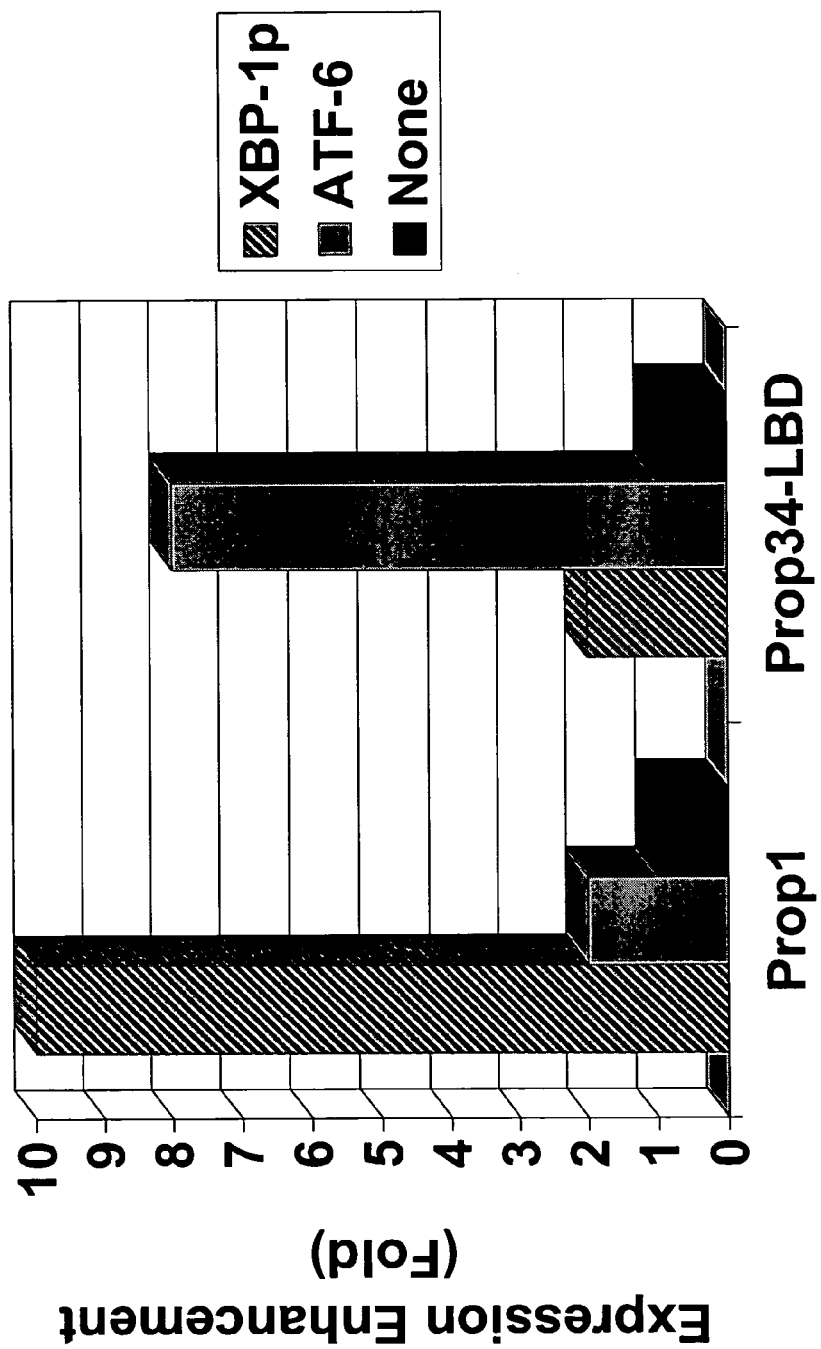
FIG. 9 demonstrates the effects of XBP1 or ATF6 on the expression of different target proteins.

FIG. 9 illustrates the effects of XBP1p or ATF6 on the expression of different target proteins. Prop1-his6-Flag or Prop34-LBD-V5-His6 in pcDNA3.1 was co-transfected with XBP1p in pSMED2 vector or ATF-6 in ptTATOP6 vector into HEK293T cells. Conditioned media harvested at 72 hr after DNA transfection were analyzed by SDS-PAGE and immunoblotting with anti-His4 antibody. Signals were quantified by densitometry as shown in FIG. 9. The results indicate that XBP1p and ATF-6 have different effects on the expression of Prop1 and Prop34-LBD. Different enhancement effects were also observed for TrkB, sFRP-1, and Agg-2 when these proteins were co-expressed with XBP1p versus ATF-6. For instance, co-expression with XBP1p increased the yield of TrkB by about 5-fold, while only about 2-fold increase was observed when TrkB was co-expressed with ATF6.

The foregoing description of the present invention provides illustration and description, but is not intended to be exhaustive or to limit the invention to the precise one disclosed. Modifications and variations consistent with the above teachings are possible or may be acquired from practice of the invention. Thus, it is noted that the scope of the invention is defined by the claims and their equivalents.

What is claimed is:

1. A mammalian cell for improved expression of a protein of interest, the mammalian cell comprising:
   at least one recombinant expression cassette encoding a protein of interest, and
   at least another recombinant expression cassette encoding an X-box binding protein 1 (XBP1) protein comprising an amino acid sequence of SEQ ID NO:6 or a functional variant thereof having at least 90% sequence identity to SEQ ID NO:6, wherein the XBP1 protein or the functional variant thereof binds the endogenous ER stress response element (ERSE) or the endogenous unfolded protein response element (UPRE) of the mammalian cell to enhance the protein folding or processing capacity of the mammalian cell,
   and wherein the improved expression of the protein of interest is a result of enhanced protein folding or processing capacity of the mammalian cell.

2. The mammalian cell according to claim 1, wherein the ratio of the total number of said at least one recombinant expression cassette to the total number of said at least another recombinant expression cassette in said cell is from 0.1:1 to 10:1.

3. The mammalian cell according to claim 2, wherein the ratio of the total number of said at least one recombinant expression cassette to the total number of said at least another recombinant expression cassette in said cell is at least 3:1.

4. A mammalian cell for improved expression of a protein of interest, said mammalian cell transfected or transduced with one or more expression vectors wherein said one or more expression vectors comprise:
   at least one recombinant expression cassette encoding a protein of interest, and
   at least another recombinant expression cassette encoding an X-box binding protein 1 (XBP1) protein comprising an amino acid sequence of SEQ ID NO:6 or a functional variant thereof having at least 90% sequence identity to SEQ ID NO:6, wherein the XBP1 protein or the functional variant thereof binds the endogenous ER stress response element (ERSE) or the endogenous unfolded protein response element (UPRE) of the mammalian cell to enhance the protein folding or processing capacity of the mammalian cell,
   and wherein the improved expression of the protein of interest is a result of enhanced protein folding or processing capacity of the mammalian cell.

5. The mammalian cell according to claim 4, wherein the molar ratio of said at least one recombinant expression cassette over said at least another recombinant expression cassette in said cell is from 0.1:1 to 10:1.

6. The mammalian cell according to claim 5, wherein the molar ratio of said at least one recombinant expression cassette over said at least another recombinant expression cassette in said cell is at least 3:1.

7. A method for improved expression of a protein of interest in a mammalian cell, said method comprising transfecting or transducing said mammalian cell with
   at least one recombinant expression cassette encoding a protein of interest, and
   at least another recombinant expression cassette encoding an X-box binding protein 1 (XBP1) protein comprising an amino acid sequence of SEQ ID NO:6 or a functional variant thereof having at least 90% sequence identity to SEQ ID NO:6, wherein the XBP1 protein or the functional variant thereof binds the endogenous ER stress response element (ERSE) or the endogenous unfolded protein response element (UPRE) of the mammalian cell to enhance the protein folding or processing capacity of the mammalian cell,
   and wherein the improved expression of the protein of interest is a result of enhanced protein folding or processing capacity of the mammalian cell.

8. The method according to claim 7, wherein the molar ratio of said at least one recombinant expression cassette over said at least another recombinant expression cassette in said cell is from 0.1:1 to 10:1.

9. The mammalian cell according to claim 1, wherein the functional variant thereof comprises an amino acid sequence at least 95% identical SEQ ID NO:6.

10. The mammalian cell according to claim 1, wherein the protein of interest is controlled by a genetically-engineered viral promoter.

11. The mammalian cell according to claim 10, wherein the genetically-engineered viral promoter is a genetically-engineered CMV promoter.

12. The mammalian cell according to claim 4, wherein the functional variant thereof comprises an amino acid sequence at least 95% identical to SEQ ID NO:6.

13. The mammalian cell according to claim 4, wherein the protein of interest is controlled by a genetically-engineered viral promoter.

14. The mammalian cell according to claim 13, wherein the genetically-engineered viral promoter is a genetically-engineered CMV promoter.

15. The method according to claim 7, wherein the functional variant thereof comprises an amino acid sequence at least 95% identical to SEQ ID NO:6.

16. The method according to claim 7, wherein the protein of interest is controlled by a genetically-engineered viral promoter.

17. The method according to claim 16, wherein the genetically-engineered viral promoter is a genetically-engineered CMV promoter.

* * * * *

SEQUENCE LISTING

```
<160> NUMBER OF SEQ ID NOS: 11

<210> SEQ ID NO 1
<211> LENGTH: 19
<212> TYPE: DNA
<213> ORGANISM: mammalian
<220> FEATURE:
<221> NAME/KEY: misc_feature
<222> LOCATION: (6)..(14)
<223> OTHER INFORMATION: n is a, c, g, or t

<400> SEQUENCE: 1
ccaatnnnnn nnnnccacg                                              19

<210> SEQ ID NO 2
<211> LENGTH: 11
<212> TYPE: DNA
<213> ORGANISM: mammalian
<220> FEATURE:
```

```
<221> NAME/KEY: misc_feature
<222> LOCATION: (6)..(6)
<223> OTHER INFORMATION: n is a, c, g, or t

<400> SEQUENCE: 2
attggnccac g                                                           11

<210> SEQ ID NO 3
<211> LENGTH: 8
<212> TYPE: DNA
<213> ORGANISM: mammalian

<400> SEQUENCE: 3 tgacgtgg                                                                8

<210> SEQ ID NO 4
<211> LENGTH: 8
<212> TYPE: DNA
<213> ORGANISM: mammalian

<400> SEQUENCE: 4 tgacgtga                                                                8

<210> SEQ ID NO 5
<211> LENGTH: 1154
<212> TYPE: DNA
<213> ORGANISM: Homo sapiens

<400> SEQUENCE: 5
atggtggtgg tggcagccgc gccgaacccg gccgacggga cccctaaagt tctgcttctg      60
tcggggcagc ccgcctccgc cgccggagcc ccggccggcc aggccctgcc gctcatggtg     120
ccagcccaga gaggggccag cccggaggca gcgagcgggg ggctgcccca ggcgcgcaag     180
cgacagcgcc tcacgcacct gagccccgag gagaaggcgc tgaggaggaa actgaaaaac     240
agagtagcag ctcagactgc cagagatcga agaaggctc gaatgagtga gctggaacag     300
caagtggtag atttagaaga agagaaccaa aaacttttgc tagaaaatca gcttttacga     360
gagaaaactc atggccttgt agttgagaac caggagttaa gacagcgctt ggggatggat     420
gccctggttg ctgaagagga ggcggaagcc aaggggaatg aagtgaggcc agtggccggg     480
tctgctgagt ccgcagcact cagactacgt gcacctctgc agcaggtgca ggcccagttg     540
tcacccctcc agaacatctc cccatggatt ctggcggtat tgactcttca gattcagagt     600
ctgatatcct gttgggcatt ctggacaact tggacccagt catgttcttc aaatgccctt     660
ccccagagcc tgccagcctg gaggagctcc cagaggtcta cccagaagga cccagttcct     720
taccagcctc cctttctctg tcagtgggga cgtcatcagc caagctggaa gccattaatg     780
aactaattcg ttttgaccac atatatacca agcccctagt cttagagata ccctctgaga     840
cagagagcca agctaatgtg gtagtgaaaa tcgaggaagc acctctcagc ccctcagaga     900
atgatcaccc tgaattcatt gtctcagtga aggaagaacc tgtagaagat gacctcgttc     960
cggagctggg tatctcaaat ctgctttcat ccagccactg cccaaagcca tcttcctgcc    1020
tactggatgc ttacagtgac tgtggatacg gggttccct ttccccattc agtgacatgt    1080
cctctctgct tggtgtaaac cattcttggg aggacacttt tgccaatgaa ctcttccccc    1140
agctgattag tgtc                                                      1154

<210> SEQ ID NO 6
<211> LENGTH: 376
```

<212> TYPE: PRT
<213> ORGANISM: Homo sapiens

<400> SEQUENCE: 6

Met Val Val Val Ala Ala Pro Asn Pro Ala Asp Gly Thr Pro Lys
1               5                   10                  15

Val Leu Leu Leu Ser Gly Gln Pro Ala Ser Ala Ala Gly Ala Pro Ala
            20                  25                  30

Gly Gln Ala Leu Pro Leu Met Val Pro Ala Gln Arg Gly Ala Ser Pro
            35                  40                  45

Glu Ala Ala Ser Gly Gly Leu Pro Gln Ala Arg Lys Arg Gln Arg Leu
50                  55                  60

Thr His Leu Ser Pro Glu Glu Lys Ala Leu Arg Arg Lys Leu Lys Asn
65                  70                  75                  80

Arg Val Ala Ala Gln Thr Ala Arg Asp Arg Lys Lys Ala Arg Met Ser
                85                  90                  95

Glu Leu Glu Gln Gln Val Val Asp Leu Glu Glu Glu Asn Gln Lys Leu
            100                 105                 110

Leu Leu Glu Asn Gln Leu Leu Arg Glu Lys Thr His Gly Leu Val Val
            115                 120                 125

Glu Asn Gln Glu Leu Arg Gln Arg Leu Gly Met Asp Ala Leu Val Ala
130                 135                 140

Glu Glu Glu Ala Glu Ala Lys Gly Asn Glu Val Arg Pro Val Ala Gly
145                 150                 155                 160

Ser Ala Glu Ser Ala Ala Gly Ala Gly Pro Val Val Thr Pro Pro Glu
                165                 170                 175

His Leu Pro Met Asp Ser Gly Gly Ile Asp Ser Ser Asp Ser Glu Ser
            180                 185                 190

Asp Ile Leu Leu Gly Ile Leu Asp Asn Leu Asp Pro Val Met Phe Phe
            195                 200                 205

Lys Cys Pro Ser Pro Glu Pro Ala Ser Leu Glu Glu Leu Pro Glu Val
            210                 215                 220

Tyr Pro Glu Gly Pro Ser Ser Leu Pro Ala Ser Leu Ser Leu Ser Val
225                 230                 235                 240

Gly Thr Ser Ser Ala Lys Leu Glu Ala Ile Asn Glu Leu Ile Arg Phe
                245                 250                 255

Asp His Ile Tyr Thr Lys Pro Leu Val Leu Glu Ile Pro Ser Glu Thr
            260                 265                 270

Glu Ser Gln Ala Asn Val Val Lys Ile Glu Ala Pro Leu Ser
            275                 280                 285

Pro Ser Glu Asn Asp His Pro Glu Phe Ile Val Ser Val Lys Glu Glu
290                 295                 300

Pro Val Glu Asp Asp Leu Val Pro Glu Leu Gly Ile Ser Asn Leu Leu
305                 310                 315                 320

Ser Ser Ser His Cys Pro Lys Pro Ser Ser Cys Leu Leu Asp Ala Tyr
                325                 330                 335

Ser Asp Cys Gly Tyr Gly Gly Ser Leu Ser Pro Phe Ser Asp Met Ser
            340                 345                 350

Ser Leu Leu Gly Val Asn His Ser Trp Glu Asp Thr Phe Ala Asn Glu
            355                 360                 365

Leu Phe Pro Gln Leu Ile Ser Val
            370                 375

<210> SEQ ID NO 7

```
<211> LENGTH: 1128
<212> TYPE: DNA
<213> ORGANISM: Homo sapiens

<400> SEQUENCE: 7
atggtggtgg tggcagccgc gccgaacccg gccgacggga cccctaaagt tctgcttctg      60
tcggggcagc cgcctccgc cgccggagcc ccggccggcc aggccctgcc gctcatggtg     120
ccagcccaga gaggggccag cccggaggca gcgagcgggg ggctgcccca ggcgcgcaag     180
cgacagcgcc tcacgcacct gagccccgag gagaaggcgc tgaggaggaa actgaaaaac     240
agagtagcag ctcagactgc cagagatcga agaaggctc gaatgagtga ctggaacag      300
caagtggtag atttagaaga agagaaccaa aaacttttgc tagaaaatca gcttttacga     360
gagaaaactc atggccttgt agttgagaac caggagttaa cagcgctt ggggatggat      420
gccctggttg ctgaagagga ggcggaagcc aaggggaatg aagtgaggcc agtggccggg     480
tctgctgagt ccgcagcagg tgcaggccca gttgtcaccc ctccagaaca tctcccccatg   540
gattctggcg gtattgactc ttcagattca gagtctgata tcctgttggg cattctggac     600
aacttggacc cagtcatgtt cttcaaatgc ccttccccag agcctgccag cctggaggag    660
ctcccagagg tctacccaga aggacccagt tccttaccag cctccctttc tctgtcagtg    720
gggacgtcat cagccaagct ggaagccatt aatgaactaa ttcgttttga ccacatatat    780
accaagcccc tagtcttaga gatacccttct gagacagaga gccaagctaa tgtggtagtg   840
aaaatcgagg aagcacctct cagcccctca gagaatgatc accctgaatt cattgtctca    900
gtgaaggaag aacctgtaga agatgacctc gttccggagc tgggtatctc aaatctgctt    960
tcatccagcc actgcccaaa gccatcttcc tgcctactgg atgcttacag tgactgtgga   1020
tacgggggtt ccctttcccc attcagtgac atgtcctctc tgcttggtgt aaaccattct   1080
tgggaggaca cttttgccaa tgaactcttt ccccagctga ttagtgtc                1128

<210> SEQ ID NO 8
<211> LENGTH: 2010
<212> TYPE: DNA
<213> ORGANISM: Homo sapiens

<400> SEQUENCE: 8
atgggggagc cggctggggt tgccggcacc atggagtcac ttttagccc gggactcttt      60
cacaggctgg atgaagattg ggattctgct ctctttgctg aacttggtta tttcacagac    120
actgatgagc tgcaattgga agcagcaaat gagacgtatg aaaacaattt tgataatctt    180
gattttgatt tggatttgtt accttgggag tcagacattt gggacatcaa caaccaaatc    240
tgtacagtta aagatattaa ggcagaaccc cagccacttt ctccagcctc ctcaagttat    300
tcagtctcat ctcctcggtc agtggactct tattcttcaa ctcagcatgt tcctgaggag    360
ttggatttgt cttctagttc tcagatgtct ccccttttcct tatatggtga aaactctaat    420
agtctctctt caccggagcc actgaaggaa gataagcctg tcactggttc taggaacaag    480
actgaaaatg gactgactcc aaagaaaaaa attcaggtga attcaaaacc ttcaattcag    540
cccaagcctt tattgcttcc agcagcaccc aagactcaaa caaactccag tgttccagca    600
aaaaccatca ttattcagac agtaccaacg cttatgccat ggcaaagca gcaaccaatt     660
atcagtttac aacctgcacc cactaaaggc cagacggttt tgctgtctca gcctactgtg    720
gtacaacttc aagcacctgg agttctgccc tctgctcagc cagtccttgc tgttgctggg    780
ggagtcacac agctccctaa tcacgtggtg aatgtggtac cagccccttc agcgaatagc    840
```

```
ccagtgaatg gaaactttc cgtgactaaa cctgtcctac aaagtaccat gagaaatgtc      900
ggttcagata ttgctgtgct aaggagacag caacgtatga taaaaaatcg agaatccgct     960
tgtcagtctc gcaagaagaa gaaagaatat atgctagggt tagaggcgag attaaaggct    1020
gccctctcag aaaacgagca actgaagaaa gaaaatggaa cactgaagcg gcagctggat    1080
gaagttgtgt cagagaacca gaggcttaaa gtccctagtc aaagcgaag agttgtctgt     1140
gtgatgatag tattggcatt tataatactg aactatggac ctatgagcat gttggaacag    1200
gattccagga gaatgaaccc tagtgtggga cctgcaaatc aaaggaggca ccttctagga    1260
ttttctgcta aagaggcaca ggacacatca gatggtatta tccagaaaaa cagctacaga    1320
tatgatcatt ctgtttcaaa tgacaaagcc ctgatggtgc taactgaaga accattgctt    1380
tacattcccc cacctccttg tcagcccta attaatacaa cagagtctct caggttaaat     1440
catgaacttc gaggatgggt tcatagacat gaagtagaaa ggaccaagtc tagaagaatg    1500
acaaataatc aacagaaaac ccgtattctt cagggtgttg tggaacaggg ctcaaattct    1560
cagctgatgg ctgttcaata cacagaaacc actagtagta tcagcaggaa ctcagggagt    1620
gagctacaag tgtattatgc ttcacccaga agttatcaag actttttga agccatccgc     1680
agaaggggag acacatttta tgttgtgtca tttcgaaggg atcacctgct gttaccagct    1740
accacccata caagaccac aagaccaaaa atgtcaattg tgttaccagc aataaacata     1800
aatgagaatg tgatcaatgg gcaggactac gaagtgatga tgcagattga ctgtcaggtg    1860
atggacacca ggatcctcca tatcaaaagt tcgtcggttc ctccttacct ccagatcag    1920
cagaggaatc aaaccaacac cttctttggc tcccctcccg cagccacaga ggcaacccac    1980
gttgtcagca ccatccctga gtcattacaa                                    2010
```

<210> SEQ ID NO 9
<211> LENGTH: 670
<212> TYPE: PRT
<213> ORGANISM: Homo sapiens

<400> SEQUENCE: 9

```
Met Gly Glu Pro Ala Gly Val Ala Gly Thr Met Glu Ser Pro Phe Ser
1               5                  10                  15

Pro Gly Leu Phe His Arg Leu Asp Glu Asp Trp Asp Ser Ala Leu Phe
            20                  25                  30

Ala Glu Leu Gly Tyr Phe Thr Asp Thr Asp Glu Leu Gln Leu Glu Ala
        35                  40                  45

Ala Asn Glu Thr Tyr Glu Asn Asn Phe Asp Asn Leu Asp Phe Asp Leu
    50                  55                  60

Asp Leu Leu Pro Trp Glu Ser Asp Ile Trp Asp Ile Asn Asn Gln Ile
65                  70                  75                  80

Cys Thr Val Lys Asp Ile Lys Ala Glu Pro Gln Pro Leu Ser Pro Ala
                85                  90                  95

Ser Ser Ser Tyr Ser Val Ser Ser Pro Arg Ser Val Asp Ser Tyr Ser
            100                 105                 110

Ser Thr Gln His Val Pro Glu Glu Leu Asp Leu Ser Ser Ser Ser Gln
        115                 120                 125

Met Ser Pro Leu Ser Leu Tyr Gly Glu Asn Ser Asn Ser Leu Ser Ser
    130                 135                 140

Pro Glu Pro Leu Lys Glu Asp Lys Pro Val Thr Gly Ser Arg Asn Lys
145                 150                 155                 160
```

-continued

```
Thr Glu Asn Gly Leu Thr Pro Lys Lys Ile Gln Val Asn Ser Lys
                165                 170                 175

Pro Ser Ile Gln Pro Lys Pro Leu Leu Leu Pro Ala Ala Pro Lys Thr
            180                 185                 190

Gln Thr Asn Ser Ser Val Pro Ala Lys Thr Ile Ile Gln Thr Val
            195                 200                 205

Pro Thr Leu Met Pro Leu Ala Lys Gln Gln Pro Ile Ile Ser Leu Gln
    210                 215                 220

Pro Ala Pro Thr Lys Gly Gln Thr Val Leu Leu Ser Gln Pro Thr Val
225                 230                 235                 240

Val Gln Leu Gln Ala Pro Gly Val Leu Pro Ser Ala Gln Pro Val Leu
                245                 250                 255

Ala Val Ala Gly Gly Val Thr Gln Leu Pro Asn His Val Val Asn Val
                260                 265                 270

Val Pro Ala Pro Ser Ala Asn Ser Pro Val Asn Gly Lys Leu Ser Val
                275                 280                 285

Thr Lys Pro Val Leu Gln Ser Thr Met Arg Asn Val Gly Ser Asp Ile
    290                 295                 300

Ala Val Leu Arg Arg Gln Gln Arg Met Ile Lys Asn Arg Glu Ser Ala
305                 310                 315                 320

Cys Gln Ser Arg Lys Lys Lys Lys Glu Tyr Met Leu Gly Leu Glu Ala
                325                 330                 335

Arg Leu Lys Ala Ala Leu Ser Glu Asn Glu Gln Leu Lys Lys Glu Asn
                340                 345                 350

Gly Thr Leu Lys Arg Gln Leu Asp Glu Val Val Ser Glu Asn Gln Arg
            355                 360                 365

Leu Lys Val Pro Ser Pro Lys Arg Arg Val Val Cys Val Met Ile Val
    370                 375                 380

Leu Ala Phe Ile Ile Leu Asn Tyr Gly Pro Met Ser Met Leu Glu Gln
385                 390                 395                 400

Asp Ser Arg Arg Met Asn Pro Ser Val Gly Pro Ala Asn Gln Arg Arg
                405                 410                 415

His Leu Leu Gly Phe Ser Ala Lys Glu Ala Gln Asp Thr Ser Asp Gly
            420                 425                 430

Ile Ile Gln Lys Asn Ser Tyr Arg Tyr Asp His Ser Val Ser Asn Asp
        435                 440                 445

Lys Ala Leu Met Val Leu Thr Glu Glu Pro Leu Leu Tyr Ile Pro Pro
    450                 455                 460

Pro Pro Cys Gln Pro Leu Ile Asn Thr Thr Glu Ser Leu Arg Leu Asn
465                 470                 475                 480

His Glu Leu Arg Gly Trp Val His Arg His Glu Val Glu Arg Thr Lys
                485                 490                 495

Ser Arg Arg Met Thr Asn Asn Gln Gln Lys Thr Arg Ile Leu Gln Gly
            500                 505                 510

Val Val Glu Gln Gly Ser Asn Ser Gln Leu Met Ala Val Gln Tyr Thr
        515                 520                 525

Glu Thr Thr Ser Ser Ile Ser Arg Asn Ser Gly Ser Glu Leu Gln Val
    530                 535                 540

Tyr Tyr Ala Ser Pro Arg Ser Tyr Gln Asp Phe Phe Glu Ala Ile Arg
545                 550                 555                 560

Arg Arg Gly Asp Thr Phe Tyr Val Val Ser Phe Arg Arg Asp His Leu
                565                 570                 575

Leu Leu Pro Ala Thr Thr His Asn Lys Thr Thr Arg Pro Lys Met Ser
```

```
                        580                 585                 590
Ile Val Leu Pro Ala Ile Asn Ile Asn Glu Asn Val Ile Asn Gly Gln
            595                 600                 605

Asp Tyr Glu Val Met Met Gln Ile Asp Cys Gln Val Met Asp Thr Arg
            610                 615                 620

Ile Leu His Ile Lys Ser Ser Val Pro Tyr Leu Arg Asp Gln
625                 630                 635                 640

Gln Arg Asn Gln Thr Asn Thr Phe Phe Gly Ser Pro Ala Ala Thr
                645                 650                 655

Glu Ala Thr His Val Val Ser Thr Ile Pro Glu Ser Leu Gln
            660                 665                 670

<210> SEQ ID NO 10
<211> LENGTH: 356
<212> TYPE: PRT
<213> ORGANISM: Homo sapiens

<400> SEQUENCE: 10

Met Glu Ala Ala Pro Gly Pro Pro Trp Pro Leu Leu Leu Leu
1               5                   10                  15

Leu Leu Leu Leu Ala Leu Cys Gly Cys Pro Ala Pro Ala Ala Ala Ser
            20                  25                  30

Pro Leu Leu Leu Phe Ala Asn Arg Arg Asp Val Arg Leu Val Asp Ala
        35                  40                  45

Gly Gly Val Lys Leu Glu Ser Thr Ile Val Val Ser Gly Leu Glu Asp
    50                  55                  60

Ala Ala Ala Val Asp Phe Gln Phe Ser Lys Gly Ala Val Tyr Trp Thr
65                  70                  75                  80

Asp Val Ser Glu Glu Ala Ile Lys Gln Thr Tyr Leu Asn Gln Thr Gly
                85                  90                  95

Ala Ala Val Gln Asn Val Val Ile Ser Gly Leu Val Ser Pro Asp Gly
            100                 105                 110

Leu Ala Cys Asp Trp Val Gly Lys Lys Leu Tyr Trp Thr Asp Ser Glu
        115                 120                 125

Thr Asn Arg Ile Glu Val Ala Asn Leu Asn Gly Thr Ser Arg Lys Val
    130                 135                 140

Leu Phe Trp Gln Asp Leu Asp Gln Pro Arg Ala Ile Ala Leu Asp Pro
145                 150                 155                 160

Ala His Gly Tyr Met Tyr Trp Thr Asp Trp Gly Glu Thr Pro Arg Ile
                165                 170                 175

Glu Arg Ala Gly Met Asp Gly Ser Thr Arg Lys Ile Ile Val Asp Ser
            180                 185                 190

Asp Ile Tyr Trp Pro Asn Gly Leu Thr Ile Asp Leu Glu Glu Gln Lys
        195                 200                 205

Leu Tyr Trp Ala Asp Ala Lys Leu Ser Phe Ile His Arg Ala Asn Leu
    210                 215                 220

Asp Gly Ser Phe Arg Gln Lys Val Val Glu Gly Ser Leu Thr His Pro
225                 230                 235                 240

Phe Ala Leu Thr Leu Ser Gly Asp Thr Leu Tyr Trp Thr Asp Trp Gln
                245                 250                 255

Thr Arg Ser Ile His Ala Cys Asn Lys Arg Thr Gly Gly Lys Arg Lys
            260                 265                 270

Glu Ile Leu Ser Ala Leu Tyr Ser Pro Met Asp Ile Gln Val Leu Ser
        275                 280                 285
```

```
Gln Glu Arg Gln Pro Phe Phe His Thr Arg Cys Glu Asp Asn Gly
    290                 295                 300
Gly Cys Ser His Leu Cys Leu Leu Ser Pro Ser Glu Pro Phe Tyr Thr
305                 310                 315                 320
Cys Ala Cys Pro Thr Gly Val Gln Leu Gln Asp Asn Gly Arg Thr Cys
                325                 330                 335
Lys Ala Gly Ala Glu His His His His His His Asp Tyr Lys Asp Asp
                340                 345                 350
Asp Asp Lys Ile
            355

<210> SEQ ID NO 11
<211> LENGTH: 800
<212> TYPE: PRT
<213> ORGANISM: Homo sapiens

<400> SEQUENCE: 11

Met Glu Thr Asp Thr Leu Leu Leu Trp Val Leu Leu Leu Trp Val Pro
1               5                   10                  15
Gly Ser Thr Gly Asp Gly Ser Thr Ser Pro Val Trp Trp Asn Ser Val
                20                  25                  30
Pro Glu Ala Phe Leu Val Phe Thr Ser Arg Ala Ala Ile His Arg Ile
                35                  40                  45
Ser Leu Glu Thr Asn Asn Asp Val Ala Ile Pro Leu Thr Gly Val
    50                  55                  60
Lys Glu Ala Ser Ala Leu Asp Phe Asp Val Ser Asn Asn His Ile Tyr
65                  70                  75                  80
Trp Thr Asp Val Ser Leu Lys Thr Ile Ser Arg Ala Phe Met Asn Gly
                85                  90                  95
Ser Ser Val Glu His Val Val Glu Phe Gly Leu Asp Tyr Pro Glu Gly
                100                 105                 110
Met Ala Val Asp Trp Met Gly Lys Asn Leu Tyr Trp Ala Asp Thr Gly
                115                 120                 125
Thr Asn Arg Ile Glu Val Ala Arg Leu Asp Gly Gln Phe Arg Gln Val
    130                 135                 140
Leu Val Trp Arg Asp Leu Asp Asn Pro Arg Ser Leu Ala Leu Asp Pro
145                 150                 155                 160
Thr Lys Gly Tyr Ile Tyr Trp Thr Glu Trp Gly Gly Lys Pro Arg Ile
                165                 170                 175
Val Arg Ala Phe Met Asp Gly Thr Asn Cys Met Thr Leu Val Asp Lys
                180                 185                 190
Val Gly Arg Ala Asn Asp Leu Thr Ile Asp Tyr Ala Asp Gln Arg Leu
                195                 200                 205
Tyr Trp Thr Asp Leu Asp Thr Asn Met Ile Glu Ser Ser Asn Met Leu
    210                 215                 220
Gly Gln Glu Arg Val Val Ile Ala Asp Asp Leu Pro His Pro Phe Gly
225                 230                 235                 240
Leu Thr Gln Tyr Ser Asp Tyr Ile Tyr Trp Thr Asp Trp Asn Leu His
                245                 250                 255
Ser Ile Glu Arg Ala Asp Lys Thr Ser Gly Arg Asn Arg Thr Leu Ile
                260                 265                 270
Gln Gly His Leu Asp Phe Val Met Asp Ile Leu Val Phe His Ser Ser
    275                 280                 285
Arg Gln Asp Gly Leu Asn Asp Cys Met His Asn Asn Gly Gln Cys Gly
    290                 295                 300
```

-continued

```
Gln Leu Cys Leu Ala Ile Pro Gly Gly His Arg Cys Gly Cys Ala Ser
305                 310                 315                 320

His Tyr Thr Leu Asp Pro Ser Ser Arg Asn Cys Ser Pro Pro Thr Thr
            325                 330                 335

Phe Leu Leu Phe Ser Gln Lys Ser Ala Ile Ser Arg Met Ile Pro Asp
                340                 345                 350

Asp Gln His Ser Pro Asp Leu Ile Leu Pro Leu His Gly Leu Arg Asn
            355                 360                 365

Val Lys Ala Ile Asp Tyr Asp Pro Leu Asp Lys Phe Ile Tyr Trp Val
370                 375                 380

Asp Gly Arg Gln Asn Ile Lys Arg Ala Lys Asp Asp Gly Thr Gln Pro
385                 390                 395                 400

Phe Val Leu Thr Ser Leu Ser Gln Gly Gln Asn Pro Asp Arg Gln Pro
                405                 410                 415

His Asp Leu Ser Ile Asp Ile Tyr Ser Arg Thr Leu Phe Trp Thr Cys
            420                 425                 430

Glu Ala Thr Asn Thr Ile Asn Val His Arg Leu Ser Gly Glu Ala Met
            435                 440                 445

Gly Val Val Leu Arg Gly Asp Arg Asp Lys Pro Arg Ala Ile Val Val
450                 455                 460

Asn Ala Glu Arg Gly Tyr Leu Tyr Phe Thr Asn Met Gln Asp Arg Ala
465                 470                 475                 480

Ala Lys Ile Glu Arg Ala Ala Leu Asp Gly Thr Glu Arg Glu Val Leu
                485                 490                 495

Phe Thr Thr Gly Leu Ile Arg Pro Val Ala Leu Val Val Asp Asn Thr
                500                 505                 510

Leu Gly Lys Leu Phe Trp Val Asp Ala Asp Leu Lys Arg Ile Glu Ser
            515                 520                 525

Cys Asp Leu Ser Gly Ala Asn Arg Leu Thr Leu Glu Asp Ala Asn Ile
530                 535                 540

Val Gln Pro Leu Gly Leu Thr Ile Leu Gly Lys His Leu Tyr Trp Ile
545                 550                 555                 560

Asp Arg Gln Gln Gln Met Ile Glu Arg Val Glu Lys Thr Thr Gly Asp
                565                 570                 575

Lys Arg Thr Arg Ile Gln Gly Arg Val Ala His Leu Thr Gly Ile His
            580                 585                 590

Ala Val Glu Glu Val Ser Leu Glu Glu Phe Ser Ala His Pro Cys Ala
            595                 600                 605

Arg Asp Asn Gly Gly Cys Ser His Ile Cys Ile Ala Lys Gly Asp Gly
610                 615                 620

Thr Pro Arg Cys Ser Cys Pro Val His Leu Val Leu Leu Gln Asn Leu
625                 630                 635                 640

Leu Thr Cys Gly Glu Pro Pro Thr Cys Ser Pro Asp Gln Phe Ala Cys
                645                 650                 655

Ala Thr Gly Glu Ile Asp Cys Ile Pro Gly Ala Trp Arg Cys Asp Gly
                660                 665                 670

Phe Pro Glu Cys Asp Asp Gln Ser Asp Glu Glu Gly Cys Pro Val Cys
            675                 680                 685

Ser Ala Ala Gln Phe Pro Cys Ala Arg Gly Gln Cys Val Asp Leu Arg
            690                 695                 700

Leu Arg Cys Asp Gly Glu Ala Asp Cys Gln Asp Arg Ser Asp Glu Ala
705                 710                 715                 720
```

-continued

```
Asp Cys Asp Ala Ile Cys Leu Pro Asn Gln Phe Arg Cys Ala Ser Gly
            725                 730                 735

Gln Cys Val Leu Ile Lys Gln Gln Cys Asp Ser Phe Pro Asp Cys Ile
            740                 745                 750

Asp Gly Ser Asp Glu Leu Met Cys Glu Ile Thr Lys Pro Pro Ser Arg
        755                 760                 765

Pro Leu Glu Ser Arg Gly Pro Phe Glu Gly Lys Pro Ile Pro Asn Pro
    770                 775                 780

Leu Leu Gly Leu Asp Ser Thr Arg Thr Gly His His His His His His
785             790                 795                 800
```